(12) United States Patent
Campbell et al.

(10) Patent No.: US 8,888,749 B2
(45) Date of Patent: Nov. 18, 2014

(54) SPRAY FOR FLUENT MATERIALS

(75) Inventors: Patrick Kenneth Campbell, Wayland, MA (US); Arthur J. Driscoll, Reading, MA (US); Tom Guest, Franklin, MA (US)

(73) Assignee: Confluent Surgical, Inc., Bedford, MA (US)

( * ) Notice: Subject to any disclaimer, the term of this patent is extended or adjusted under 35 U.S.C. 154(b) by 0 days.

(21) Appl. No.: 13/411,718

(22) Filed: Mar. 5, 2012

(65) Prior Publication Data

US 2012/0165727 A1    Jun. 28, 2012

Related U.S. Application Data

(63) Continuation of application No. 12/610,919, filed on Nov. 2, 2009, now Pat. No. 8,152,777, which is a continuation of application No. 11/053,084, filed on Feb. 8, 2005, now Pat. No. 7,611,494.

(51) Int. Cl.
*A61M 5/00* (2006.01)
*A61B 17/00* (2006.01)

(52) U.S. Cl.
CPC . *A61B 17/00491* (2013.01); *A61B 2017/00495* (2013.01)
USPC .......................................................... 604/191

(58) Field of Classification Search
CPC .................. A61B 17/0057; A61B 2017/0065; A61B 18/06; A61B 17/00491; A61B 2017/00495; A61M 35/00; A61M 15/009; A61M 25/0021; A61M 25/0071; A61M 5/19; A61M 2005/1787; A61M 5/31596; A61M 2202/0476; A61M 2210/0693; B05B 11/3084; B05B 7/0876; B05B 1/26; B05B 7/065; B05B 7/08; B05B 7/0807; B05C 17/00516

USPC ............................................................. 604/191
See application file for complete search history.

(56) References Cited

U.S. PATENT DOCUMENTS 3,161,602 A    12/1964 Herbig
3,242,237 A     3/1966 Belak et al.
(Continued)

FOREIGN PATENT DOCUMENTS

EP    0443743    8/1991
JP    3025028    3/1996
(Continued)

OTHER PUBLICATIONS

Allen et al., "Pharmacokinetics of Stealth Venus Conventional Liposomes: Effect of Dose." Biochimica et BioDhvsica Acta. 1068: 133-144 (1991).

(Continued)

*Primary Examiner* — Jason Flick
(74) *Attorney, Agent, or Firm* — Carter, DeLuca, Farrell & Schmidt, LLP

(57) ABSTRACT

Certain embodiments relate to a sprayer or other medical apparatus for applying a biocompatible coating in situ. Such an apparatus may have a first conduit connected to a first exit opening and a second conduit connected to a second exit opening to deliver a first composition through the first conduit and a second composition through the second conduit to mix the first composition and the second composition outside both the first conduit and the second conduit. The first composition may be, e.g., a precursor to a material formed after the mixing of the first composition and the second composition. The first exit opening and the second exit opening may be approximately adjacent to each other and define an angle that is less than about 140 degrees.

7 Claims, 13 Drawing Sheets

(56) References Cited

U.S. PATENT DOCUMENTS

| | | | |
|---|---|---|---|
| 3,423,894 | A | 1/1969 | Richardson |
| 3,640,741 | A | 2/1972 | Etes |
| 3,779,942 | A | 12/1973 | Bolles |
| 3,865,108 | A | 2/1975 | Hartop |
| 3,991,766 | A | 11/1976 | Schmitt et al. |
| 3,992,562 | A | 11/1976 | Denzinger et al. |
| 4,001,391 | A | 1/1977 | Feinstone et al. |
| 4,002,173 | A | 1/1977 | Manning et al. |
| 4,014,335 | A | 3/1977 | Arnold |
| 4,207,893 | A | 6/1980 | Michaels |
| 4,369,229 | A | 1/1983 | Shah |
| 4,530,840 | A | 7/1985 | Tice et al. |
| 4,597,970 | A | 7/1986 | Sharma et al. |
| 4,631,055 | A | 12/1986 | Redl et al. |
| 4,735,616 | A | 4/1988 | Eibl et al. |
| 4,741,872 | A | 5/1988 | DeLuca et al. |
| 4,826,945 | A | 5/1989 | Cohn et al. |
| 4,828,857 | A | 5/1989 | Sharma et al. |
| 4,846,405 | A | 7/1989 | Zimmermann |
| 4,902,281 | A | 2/1990 | Avoy |
| 4,938,763 | A | 7/1990 | Dunn et al. |
| 5,100,992 | A | 3/1992 | Cohn et al. |
| 5,160,745 | A | 11/1992 | DeLuca et al. |
| 5,171,148 | A | 12/1992 | Wasserman et al. |
| 5,198,220 | A | 3/1993 | Damani |
| 5,322,510 | A | 6/1994 | Lindner et al. |
| 5,341,993 | A | 8/1994 | Haber et al. |
| 5,368,563 | A | 11/1994 | Lonneman et al. |
| 5,410,016 | A | 4/1995 | Hubbell et al. |
| 5,464,396 | A | 11/1995 | Barta et al. |
| 5,474,540 | A | 12/1995 | Miller et al. |
| 5,505,704 | A | 4/1996 | Pawelka et al. |
| 5,565,215 | A | 10/1996 | Gref et al. |
| 5,582,596 | A | 12/1996 | Fukunaga et al. |
| 5,589,194 | A | 12/1996 | Tsuei et al. |
| 5,605,541 | A | 2/1997 | Holm |
| 5,618,563 | A | 4/1997 | Berde et al. |
| 5,650,173 | A | 7/1997 | Ramstack et al. |
| 5,693,341 | A | 12/1997 | Schroeder et al. |
| 5,740,965 | A * | 4/1998 | Miyagi et al. ................. 239/423 |
| 5,759,169 | A | 6/1998 | Marx |
| 5,874,500 | A | 2/1999 | Rhee et al. |
| 6,065,645 | A | 5/2000 | Sawhney et al. |
| 6,152,943 | A | 11/2000 | Sawhney |
| 6,165,201 | A * | 12/2000 | Sawhney et al. .............. 606/214 |
| 6,179,862 | B1 | 1/2001 | Sawhney |
| 6,206,905 | B1 | 3/2001 | Holm et al. |
| 6,379,373 | B1 | 4/2002 | Sawhney et al. |
| 6,454,786 | B1 | 9/2002 | Holm et al. |
| 6,514,534 | B1 | 2/2003 | Sawhney |
| 6,527,749 | B1 * | 3/2003 | Roby et al. .................... 604/191 |
| 6,566,406 | B1 | 5/2003 | Pathak et al. |
| 6,605,294 | B2 | 8/2003 | Sawhney |
| 6,610,033 | B1 | 8/2003 | Melanson et al. |
| 6,632,457 | B1 | 10/2003 | Sawhney |
| 6,673,093 | B1 | 1/2004 | Sawhney |
| 6,689,148 | B2 | 2/2004 | Sawhney et al. |
| 6,703,047 | B2 | 3/2004 | Sawhney et al. |
| 6,783,514 | B2 | 8/2004 | Tovey et al. |
| 6,818,018 | B1 | 11/2004 | Sawhney |
| 6,887,974 | B2 | 5/2005 | Pathak |
| 2003/0012734 | A1 | 1/2003 | Pathak et al. |
| 2003/0077242 | A1 | 4/2003 | Sawhney |
| 2003/0077272 | A1 | 4/2003 | Pathak |
| 2003/0108511 | A1 | 6/2003 | Sawhney |
| 2003/0162841 | A1 | 8/2003 | Pathak et al. |
| 2004/0002456 | A1 | 1/2004 | Pathak |
| 2004/0009205 | A1 | 1/2004 | Sawhney |
| 2004/0023842 | A1 | 2/2004 | Pathak et al. |
| 2004/0033264 | A1 | 2/2004 | Sawhney |
| 2005/0080445 | A1 | 4/2005 | Sawhney et al. |

FOREIGN PATENT DOCUMENTS

| | | |
|---|---|---|
| WO | WO 96/39212 | 12/1996 |
| WO | WO 00/15117 | 3/2000 |
| WO | WO 00/37178 | 6/2000 |

OTHER PUBLICATIONS

Allen et al., "Lipsomes Containing Synthetic Lipid Derivatives of Poly(ethylene glycol) Show Prolonged Circulation Half-Lives in Vivo," Biochimica et Bioohvsica Acta. 1066:29-36 (1991).

Bailey et al., "Synthesis of Polymezized Vesicles with Hydrolyzable Linkages," Macromolecules. 25:3-11 (1992).

Bhatia et al., "The Effect of Site of Implantation and Animal Age on Properties of Polydioxanone Pins," J. Biomater. Sci., Polymer, Edn., Bamform, CH., Bamford, C.H., et al., eds. 6(5): 435-446 (1994).

Dong et al., "Dextran Permeation Through Poly (N-Isopropylacrylamide) Hydrogels," J. Biomater. Sci., Polymer Edn., Bamford, C.H. eds. 5(5): 473-484 (1994).

Edgington. "New Horizons for Stem-Cell Bioreactors" BioTechnoloev. 10: 1099-1106 (1992).

Ferland et al., "Evaluation of a sprayable polyethelene glycol adhesion barrier in a porcine efficacv model". European Society of Human Reproduction and Embrvoloev, 16(12); 2718-2723 (2001).

Ferland et al., "Evaluation of SprayGel™ Adhesion Barrier System as a Barrier for the Prevention of Adhesion Formation After Gynecological Surgery", ISGE 10. Chicago Mar. 2001.

Handbook of Common Polymers, compiled by Roff, W., J. et al., CRC Press, Cleveland, Ohio.

Jacobs et al., "A Pressure-Balanced Sprayer for of Soluble Biomaterials in Laparoscopv". ISGE 10. C (2001).

Jarret et al., "Bioabsorbable Hydrogel Tissue Barrier in Situ Gelation Kinetics," Soc. For Biomater., Transactions of $21^{st}$ Annual Meeting: 182 (1995).

Klibanov et al., "Activity of Amphipathic Poly (ethylene glycol) 5000 to Prolong the Circulation Time of Liposomes Depends on the Liposome Size and Is Unfavorable for Immunoliposome Binding to Target," Biochimica et Bioohvsica Acta. 1062:142-148 (1991).

Lasic et al., "Sterically Stabilized Liposomes: A Hypothesis on the Molecular Orgin of the Extended Circulation Times." Biochimica et Biophvsica Acta. 1070: 187-192 (1991).

Ley et al., "Endothelial, Not Hemodynamic, Differences Are Responsible for Preferential Leukocyte Rolling in Rat Mesenteric Venules." Circulation Research. 69(4): 1034-1041 (1991).

Maruyama et al., "Effect of Molecular Weight in Amphipathic Polyethyleneglycol on Prolonging the Circulation Time of Large Unilamellar Liposomes." Chem. Pharm. Bull., 39(6): 1620-1622 (1991).

Mayhew et al., "Characterization of Liposomes Prepared Using a Microemulsifier." Biochimica et Bicohvsica Acta, 775:169-174 (1984).

Nagaoka et al., "Interaction Between Blood Components and Hydrogels with Poly(oxyethylene) Chairs," Polymers As Biomaterials, Shalaby, S. W. et al., eds. Plenum Press, New York, 361-374 (1984).

Okano et al., "Effect of Hydrophilic and Hydrophobic Macrodomains on Mode of Interaction Between Block Polymer and Blood Platelets," J. Biomed. Mats. Research, 15:393-402 (1981).

Onishi et al., "Study of Dextran-Methyl methacrylate Graft Copolymer," Contempory Topics in Polymer Science, Bailey, W.J. et al., eds. Plenum Press, New York, 4:149-162 (1984).

Park, "Enzyme-Digestible Swelling Hydrogels as Platforms for Long-Term Oral Drue Deliver/: Synthesis and Characterization." Biomaterials. 9:435-441 (1988).

Park et al., Biodegradable Hydrogels for Drug Delivery, Technomic Publishing Co., Inc. Lancaster, Pennsylvania (1993).

Raud et al., "Leukocyte Rolling and Firm Adhesion in the Microcirculation." Gastroenteroloev. 104: 310-314 (1993).

Remington's Pharmaceutical Sciences, 14th Ed., J. E. Hoover et al., eds., Mack Publishing co., Easton, Pennsylvania (1970).

Sawhney et al., "Bioerodible Hydrogels Based on Photopolymerized Poly(ethene glycol)-co-poly(a-hydroxy acid) Diacrylate Macromers," Macromotecules. 26:581-587 (1993).

(56) References Cited

OTHER PUBLICATIONS

Shah. Novel Two-Phase PolymerSystem. Polymer. 28:1212-1216 C1987).

Shah, "Hydrophilic-Hydrophobic Domain Polymer systems," Water Soluble Polymers, chap. 30, Shalaby, SW. et al., eds. Amer. Chem. Soc, Washington, D.C., 467-483 (1993).

Shalaby, "Boabsorbably Polymers" Encyclopedia of Pharmaceutical Technology, Swarbrick, J. et al, eds., Marcel Dekker, Inc., New York, 1:465-476(1988).

Shalaby et al., "In Vitro and In Vivo Studies of Enzyme-Digestible Hydrogels for Oral Drug Delivery," J. Controlled Release. 19:131-144 (1992).

Silberberg, "Network Deformation in Flow:" Molecular Basis of Polymer Networks, Baumgartner, A. et al., eds., Springer-Verlag, Berlin, 42:147-151 (1989).

Smith et al., "Association reactions for poly(alkylene oxides) and poly(carboxylic acids)". Ind. Ene. Chem., 51:1361 (1959).

The Drug, The Nurse, The Patient (Including Current Drug Handbook), Falconer's 7$^{th}$ Ed. W.B. Saunders Co., Philadelphia, Pennsylvania (1974).

Torchilin et al., "Liposome-Polymer systems. Introduction of Lipsomes into a Polymer Gel and Preparation of the Polymer Gel Inside a Liposome," Polymer, Sci. U.S.S.R.. 30(10): 2307-2312 (1988).

Torchin et al., The Antibody-Linked Chelating Polymers for Nuclear Therapy and Diagnostics. Critical Reviews in Therapeutic Drue Carrier Systems. 7(4): 275-308 (1991).

Woodle et al., "Versatility in lipid compositions showing prolonged circulation with sterically stabilized lipsones", Biochimica et Biophysica Acta. 1105:193-200 (1992).

\* cited by examiner

SPRAY FOR FLUENT MATERIALS

CROSS-REFERENCE TO RELATED APPLICATIONS

This application is a continuation of U.S. application Ser. No. 12/610,919 filed Nov. 2, 2009 now U.S. Pat. No. 8,152,777, which is a continuation of U.S. application Ser. No. 11/053,084 filed Feb. 8, 2005, now U.S. Pat. No. 7,611,494, and the disclosures of each of the above-identified applications are hereby incorporated by reference in their entirety.

FIELD OF THE INVENTION

Certain aspects of the field of the invention relate generally to methods and apparatus for forming biocompatible materials, and, more particularly, to apparatus and methods using an angled tip sprayer for delivering two liquid components that form hydrogels upon mixing.

BACKGROUND OF THE INVENTION

Often during surgery, tissue may be traumatized or compromised such that it needs to be temporarily supported or isolated during the wound healing period. Materials that may be used as tissue sealants also may be used to temporarily support tissue and to seal leaks from tissue until the tissue heals. Tissue sealants that perform these functions are well known in literature and include a variety of natural and synthetic sealants including fibrin sealants, cyanoacrylate based sealants, and other synthetic sealants and polymerizable macromers.

Various types of devices have been developed that address many aspects of spraying technologies to deliver sealants. For example, U.S. Pat. No. 5,605,541 to Holm describes apparatus and methods for applying two or more components of a fibrin sealant. U.S. Pat. No. 5,368,563 to Lonneman et al. describes a sprayer assembly having angular connecting channels through which components of a fibrin sealant are discharged to cause mixing. U.S. Pat. No. 5,341,993 to Haber et al. describes a hand held sprayer having a remotely actuated spray tip. U.S. Pat. No. 4,001,391 to Feinstone et al. describes a method for spraying viscous and buttery fluids using a propellant and a pressurized container. U.S. Pat. No. 6,206,905 to Holm et al. describes a method and device for mixing the two components of a biomaterial using various tip configurations of the delivery system for mixing of the components.

SUMMARY OF THE INVENTION

Applicants have determined that when attempting to use a propellant to apply materials in a laparoscopic setting, which typically is insufflated with a gas to provide a wider field of view for the clinician, the propellant can result in excessive distension of the tissue surrounding the operative site. In addition, in the above laparoscopic context, when a sprayer is first introduced into the surgical site, for example, via a trocar tube, the ambient pressure may inadvertently charge the supply reservoirs (if the supply lines of the sprayer are not already pressurized), thereby interfering with proper dispensing of the materials into the supply lines when the clinician attempts to operate the device.

These and additional problems have been addressed by U.S. Pat. Nos. 6,152,943, 6,165,201, 6,179,862, 6,379,373, 6,673,093, and 6,689,148, which describe, inter alia, a sprayer capable of applying two or more crosslinkable precursor components to a tissue. The sprayers may have nozzles for each of the crosslinkable precursor components, and may use an annular gas flow outlet or be in communication with a gas-pressurized chamber to form a sealant when the components are mixed. Such sprayers have used nozzles with openings that are substantially parallel to each other, e.g., the openings are side-by-side in the same plane. However, it is possible to improve these devices by further reducing the potential to clog while delivering a fine, controlled amount of sealant in a stop and start motion. Any amount of clogging may be a problem because it can cause occlusion and/or divergent streams, which in turn may cause poor mixing and ultimately a poor sealant.

One way that clogging may occur is by precursor migration from spray nozzle to spray nozzle ("cross-talk" or cross-contamination). When a component is sprayed out of a nozzle or other opening, it forms a conical pattern that appears as a fan pattern when viewed two-dimensionally. And, when two or more components are sprayed from separate adjacent nozzles or openings, the fan patterns overlap to form a mixing region. However, a low-pressure area adjacent to the openings can exist in the space between the two or more overlapping fan patterns. Precursors may be pulled into the low-pressure area, where they react and clog the openings. A precursor refers to material that is reacted to be incorporated into the material. For example, a monomer is a precursor that may be reacted to be incorporated into a polymeric material. In contrast, a polymerization initiator may react to catalyze formation of a material without becoming incorporated into that material.

Another mode of clogging may be caused by surface tension. As a result, when a precursor passes through an opening, some of the precursor may tend to remain at or near the opening, and to spread around the opening. Consequently, mutually reactive precursors flowing through openings that are adjacent to each other may tend to become mixed and react at or near the openings.

Certain embodiments herein describe a solution for these problems by use of an angled applicator tip having openings that are set at an angle relative to each other. An angled tip is in contrast to a tip having the openings substantially parallel to each other. The angled tip may be created, for example, by making a first exit opening and a second exit opening approximately adjacent to each other while defining an angle between the openings that is less than about 140 degrees, e.g., see FIGS. 5 and 6. The term tip is conveniently used to denote an end portion or a projecting portion of an apparatus.

An angle between two openings may be measured by fitting a plane to each opening and measuring the angle formed by the intersection of the two planes. Thus, two openings may define the angle between them when the openings are positioned relative to each other so that there is an angle formed by the intersection of the two planes. Thus two openings that were perpendicular to each other would have an angle of 90 degrees between them. The angle between two flat surfaces is readily measured when every point of an opening falls in a single plane; for example, an opening on a flat surface is disposed in one plane. When an opening is made in a curved surface, however, it is necessary to fit a plane to the opening. The fit may be accomplished using mathematical techniques known to persons of skill in these arts. Without being bound to a particular theory of action, it is believed that the angled tip creates a low-pressure zone between spraying fan patterns of two or more components, thereby drawing the components together in the air stream beyond the tip and improving their mixing. The angled tip also creates a wall or divider between adjacent lumen openings, thereby preventing cross-talk between precursors before they enter the air stream. Further, an angled tip may be more precise and deliver a higher quality gel over the course of an application.

An advantage of placing the openings adjacent to each other is that such placement facilitates the mingling of compositions that flow through the openings. Openings that are adjacent to each other are typically separated only by a thickness of the material that defines the openings. For example, two needles may be placed adjacent to each other, with their exteriors touching. The openings may be further separated and still be considered to be adjacent. For example, two openings that are separated by a distance of less than about three times the maximum diameter of one of the openings would be adjacent to each other, e.g., see FIG. 1.

Moreover, providing a gap between the openings of an angled tip and any surrounding materials minimizes the role of surface tension. Also, defining an appropriate gas flow rate achieves both good mixing and a good gel while at the same time minimizing clogging, providing that the gas flow is balanced with the need to avoid generating a rush of air that will blow the mixed components from the target location. Minimizing cross-talk and surface tension allows a fine, controlled amount of precursors to be delivered at an appropriate air flow rate in a stop and start motion without clogging.

Some embodiments relate to apparatus and methods that enable a tissue coating comprising two or more crosslinkable fluids to be applied in situ as a spray. Some embodiments have a reduced risk of clogging of the sprayer due to cross-talk and surface tension. Some of the apparatus and methods permit spraying of polymerizable fluids having precursors in a laparoscopic environment, but adjust the pressure in the cavity to account for the introduction of propellant from the sprayer, thereby avoiding excessive distension of the tissue surrounding the operative site.

Some embodiments relate to apparatus and methods that permit spraying of polymerizable fluids in a lap aroscopic environment, but prevent material reservoirs of the sprayer from being inadvertently pressurized by the backflow of insufflation gases through the supply lines. Certain embodiments provide apparatus and methods that enable a tissue coating comprising two or more crosslinkable fluids to be applied in situ as a spray.

Certain embodiments may be accomplished by providing a sprayer with an angled tip capable of applying two or more precursors to a tissue to form a coating on the tissue surface. For example, two crosslinkable solutions, each containing one component of a co-initiating system capable of crosslinking when mixed together, may be placed in separate chambers of the sprayer. When the sprayer is activated, the emergent spray contacts tissue, resulting in mixing and crosslinking of the two solutions to form a coating (for example a hydrogel) on the tissue surface.

In certain embodiments, the sprayer comprises separate spray openings at the spraying end of separate conduits for each of two or more crosslinkable solutions, with each conduit at least partially surrounded by a separate or common gas flow outlet. The crosslinkable solutions are stored in separate compartments, e.g., a multi-cylinder syringe, and communicated under pressure to the spray openings. In the presence of gas flow through the gas flow outlets, the crosslinkable solutions are atomized and mixed in the gas flow to form a spray, which may be used to coat tissue. In an alternative embodiment, the gas flow is mixed with the crosslinkable solutions to both propel the solutions out of the spray openings and atomize the solutions.

In another embodiment, the sprayer includes a vent system that vents excess pressure from the tissue cavity to avoid excessive distention of the tissue cavity surrounding the operative site in laparoscopic applications.

In another embodiment, the supply lines include one-way valves that permit flow through the supply line in the distal direction, but prevent backflow into the compartments storing the crosslinkable solutions when the sprayer is first introduced into an insufflated tissue cavity.

In certain embodiments, the crosslinkable solutions used with the apparatus may be crosslinked using physical crosslinking, chemical crosslinking, or both. For a chemical initiation process, the two or more crosslinkable solutions may polymerize when mixed in the gas flows during spraying, thus forming an adherent coating that adheres to the tissue surface on contact. If a thermal initiating process is used, the two or more solutions may crosslink after contacting the tissue surface and warming to physiological temperatures.

Alternatively, the two or more solutions may include macromers that contain groups that demonstrate activity towards other functional groups such as amines, imines, thiols, carboxyls, isocyanates, urethanes, amides, thiocyanates, hydroxyls, etc., some of which may be naturally present in, on, or around tissue or may be optionally provided in the region as part of the instilled formulation required to effect the barrier.

Certain embodiments are directed to a medical device for applying a biocompatible material or a coating in situ comprising at least a first conduit connected to at least a first exit opening and a second conduit connected to at least a second exit opening to deliver a first composition through the first conduit and a second composition through the second conduit to mix the first composition and the second composition outside both the first conduit and the second conduit. The first composition may comprise a precursor to a material formed after the mixing of the first composition and the second composition. The first exit opening and the second exit opening may be approximately adjacent to each other and define an angle that is less than about 60, 90, 120, 140, or 150 degrees. Other embodiments include methods of using the apparatus. Methods of forming tissue adherent barriers in accordance with the principles of the present invention also are provided.

BRIEF DESCRIPTION OF THE DRAWINGS

Certain features of the invention, its nature, and various advantages will be apparent from the accompanying drawings and the following detailed description of certain embodiments, in which.

DETAILED DESCRIPTION

As already discussed, an angled applicator tip having openings that are set at an angle relative to each other may advantageously be used to dispense biocompatible materials. Further, a gas flow outlet may be positioned relative to the openings so that compositions flowing from the openings are readily removed from the area of the openings by the action of the gas. And certain flow rates may advantageously be used to reduce clogging of the openings while maintaining a consistent deposition of compositions onto a surface.

Applicators for Dispensing Compositions for Forming Biocompatible Materials In Situ in a Patient In many embodiments, a medical device applicator has a body with a distal portion. The distal portion has a distal tip with two or more openings. Each opening has a conduit for fluid connection to a source of a composition that is to be dispensed through the opening. The source may be, e.g., a chamber that is permanently or reversibly connectable to the device to be in fluid communication with the conduit. A gas source provides gas to dispense the compositions from the openings.

The gas may be used in a variety of ways to dispense the compositions. For example, the gas may be placed behind the compositions to push them through the openings. Or the gas may be forced into a chamber with the composition to mix with the composition and elevate the chamber pressure so that the gas-composition mixture is forced from the chamber when the chamber is opened. Or the gas may be directed through a gas flow outlet that surrounds, or is near, the openings for the compositions, so that the flow of the gas pulls the compositions from their openings. This latter method advantageously reduces the size of the vessel used to provide the compositions to the apparatus.

The medical device applicator sprayer may be directed to the use of multi-component crosslinkable solutions to form materials in situ in a patient, e.g., to prevent post-surgical adhesions, or as drug delivery layers. In accordance with the methods of certain embodiments, two or more crosslinkable solutions are sprayed onto tissue during, or near the completion, of surgery to form adherent coatings. Multi-component hydrogel systems suitable for such use, apparatus for dispensing such hydrogel systems, and examples of use of the inventive methods and apparatus are described.

Figure 1A:
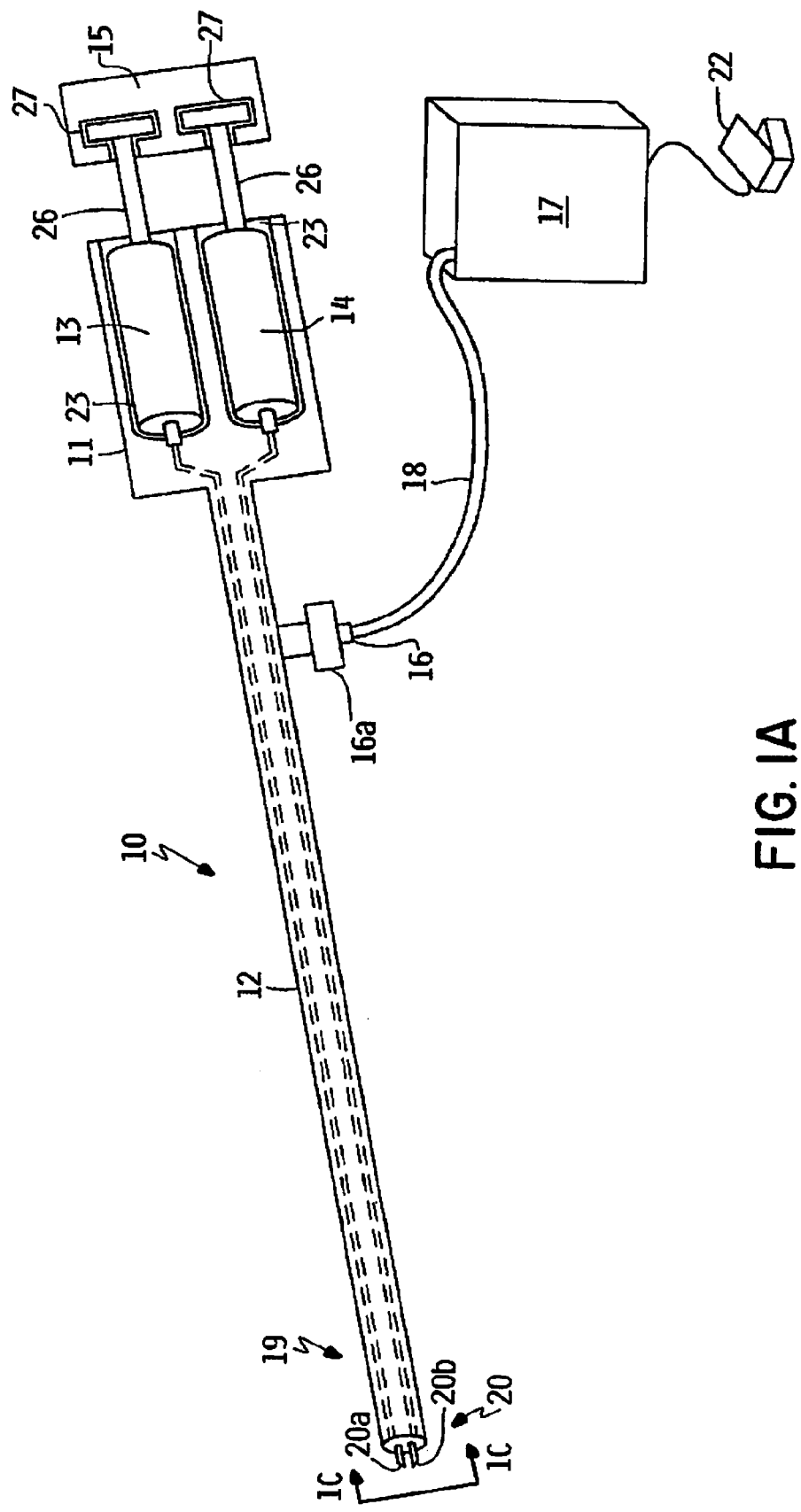
FIGS. 1A, 1B and 1C, are, respectively, a perspective view of certain embodiments of a two-fluid sprayer, a detailed view of the distal portion of the sprayer, and an end view of the distal portion of the sprayer taken along line 1C-1C of FIG. 1A.
Figure 1B:
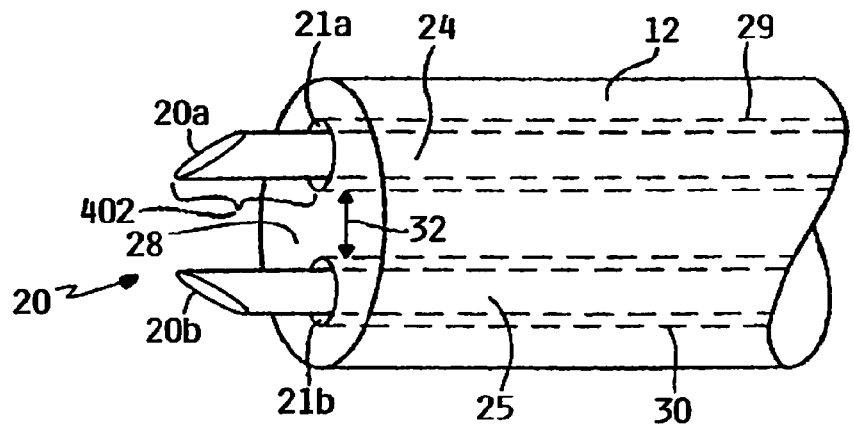
Figure 1C:
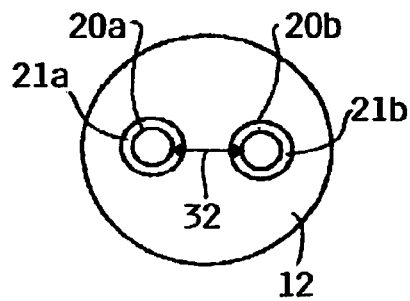

Referring now to FIGS. 1A, 1B, and 1C, an illustrative embodiment of a sprayer medical device is described. Sprayer 10 comprises body 11 having elongated barrel 12, syringes 13 and 14, actuator 15 and gas inlet port 16 coupled to compressor 17 via flexible hose 18. Distal portion 19 of sprayer 10 includes a distal tip 20, which has distal tip openings 20a and 20b. Compressor 17 supplies a gas flow, preferably compressed air or carbon dioxide, to sprayer 10 either continuously, or when activated by footpedal 22. Gas inlet port 16 may include filter 16a to remove particulate contaminants, including bacteria and other microorganisms, from the gas flow.

The gas flow outlet may be placed adjacent to, and proximal to, the openings for the compositions, as in FIG. 1, which depicts gas flow outlets 21a, 21b, and 21a', and openings 20a, 20b, 20a', and 20b' disposed in the endface of barrel 12. In this configuration, there is a gap 402 wherein gas flowing from the gas flow outlet flows past the tube that opens into an outlet, 20a, 20a', 20b. The flowing gas tends to keep the openings clear of compositions that flow out of openings 20a, 20b, 20a', and 20b'. A spacing distance between the openings provides a separation that reduces opportunities for unwanted cross-talk between the openings, as shown by element 32 in FIGS. 1A, 1B, and 1C, and by element 32' in FIG. 1D.

Body 11 includes chambers 23 into which syringes 13 and 14 are placed so that the outlets of the syringes are coupled in fluid communication with distal tip openings by way of interior conduits 24 and 25. Each of syringes 13 and 14 includes plunger 26 that may be engaged in recesses 27 of actuator 15. Accordingly, when actuator 15 is depressed, an equal volume of crosslinkable solution is dispensed from each of syringes 13 and 14. Alternatively, for some systems it may be desirable to omit actuator 15 and instead spray the crosslinkable solutions onto the tissue in a sequential fashion. In either case, sterile crosslinkable solutions may be stored separately in syringes 13 and 14, and assembled in sprayer 10 as required for a particular application.

Conduit 24 extends from the proximal end of barrel 12, where it is coupled to syringe 13, to a point a slightly beyond distal endface 28 of barrel 12, where it forms opening 20a. Conduit 24 is disposed within lumen 29 that communicates with gas inlet port 16. Gas entering sprayer 10 via gas inlet port 16 flows through the annular space defined by the exterior of conduit 24 and the interior surface of lumen 29, exiting sprayer 10 through gas flow outlet 21a. As the gas, preferably air or carbon dioxide, flows through gas flow outlet 21a, it mixes with the crosslinkable solution from syringe 13 passing through opening 20a, breaking the crosslinkable solution into fine droplets or a mist.

Likewise, conduit 25 extends from the proximal end of barrel 12, where it is coupled to syringe 14, to a point a slightly beyond distal endface 28 of barrel 12, where it forms opening 20b. Conduit 25 is disposed within lumen 30 that communicates with gas inlet port 16. Thus, gas entering sprayer 10 via gas inlet port 16 flows through the annular space defined by the exterior of conduit 25 and the interior surface of lumen 30, exiting sprayer 10 through gas flow outlet 21b. As the gas flows through gas flow outlet 21b, it mixes with the crosslinkable solution from syringe 14 passing through opening 20b, also breaking the crosslinkable solution into fine droplets or a mist.

Openings 20a and 20b are preferably arranged so that the crosslinkable droplets or mist formed by opening 20a and gas flow outlet 21a converges with that formed by opening 20b and gas flow outlet 21b to provide a spray containing a mixture of the two crosslinkable solutions. As described hereinabove, the two solutions may either crosslink on contact within the spray, or crosslink upon contacting the tissue. Openings 20a and 20b are also preferably arranged so as to minimize clogging of the distal tip 20 by premature crosslinking of the emergent fluids by cross-contamination. An aspect of minimizing the cross-contamination is the optional use of a separation distance between the openings, e.g., as shown in FIGS. 1A-1D and denoted by elements 32 and 32'.

The distal tip 20 has an angled shape that helps to reduce cross-contamination of the emergent compositions. The angled shape of the distal tip 20 is the arrangement of the openings 20a and 20b with respect to each other.

Referring to FIGS. 1A-1C, as a further alternative, instead of using footpedal 22 to regulate the gas flow, compressor 17 may be regulated with a valve (not shown) disposed on body 11 or barrel 12, that selectively diverts gas flow from lumens 29 and 30. This feature may be particularly useful when the sprayer is used in closed relatively fluid tight cavities, such as the pneumoperitoneum created during laparoscopic or pelvic surgery.

Body 11, barrel 12 and actuator 15 preferably are constructed from a plastic such as polyethylene, while conduits 24 and 25 preferably comprise a rigid material, such as stainless steel. Syringes 13 and 14 may comprise materials typically used in medical devices, while compressor 17 and flexible hose 18 may be of the type commercially available, for example, that are used with airbrushes.

In operation, sprayer 10 is coupled to compressor 17 via flexible hose 18. Syringes 13 and 14 are inserted into chambers 23 of body 11 and plungers 26 of syringes 13 and 14 are engaged in recesses 27 in actuator 15. Distal portion 19 of sprayer 10 is disposed within a body cavity, for example, intraoperatively in the abdomen or laparoscopically in the pneumoperitoneum, a few inches from tissue to be coated. Footpedal 22 is then depressed to activate compressor 17, while actuator 15 is depressed to dispense crosslinkable solutions from openings 20a and 20b. As the solutions emerge from openings 20a and 20b, they are atomized and partially or completely mixed, and directed onto the tissue to be coated. As a result of crosslinking, for example, induced by free radical or chemical crosslinking, the solutions form a film that adheres to the tissue to provide a therapeutic benefit. Alternatively, the solutions may be mixed when they contact the tissue surface.

Figure 1D:
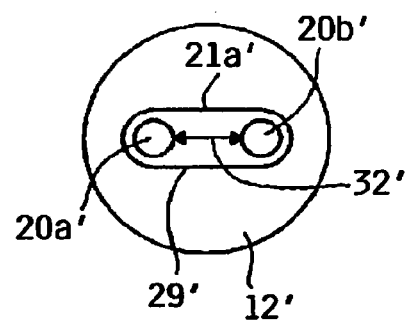
FIG. 1D is an end view of the distal portion of an alternative embodiment of the sprayer of FIG. 1A taken along line 1C-1C.

In FIG. 1D, an alternative embodiment is depicted in which barrel 12' includes openings 20a' and 20b' disposed within single gas flow outlet 21a' and gas flow lumen 29'. The first opening and the second opening are adjacent to a gas flow outlet, and the gas flow outlet surrounds at least the first opening, and, in the case of FIG. 1D, two openings. Operation of this alternative embodiment is similar to that described hereinabove, except that the crosslinkable solutions are entrained from openings 20a' and 20b' by a single stream of gas exiting gas flow outlet 21a'. In addition, the sprayer may include a valve or valves (not shown) for regulating the amount of crosslinkable solution and gas exiting openings 20a' and 20b' and gas flow outlet 21a', respectively. Such valves also may permit a jet of gas to be directed onto a targeted tissue, for example, to displace saline or body fluids to dry or clean the target tissue prior to instillation of the hydrogel barrier. Separation distance 32' provides a separation between the openings to reduce unwanted cross-contamination between the openings.

Figure 2A:
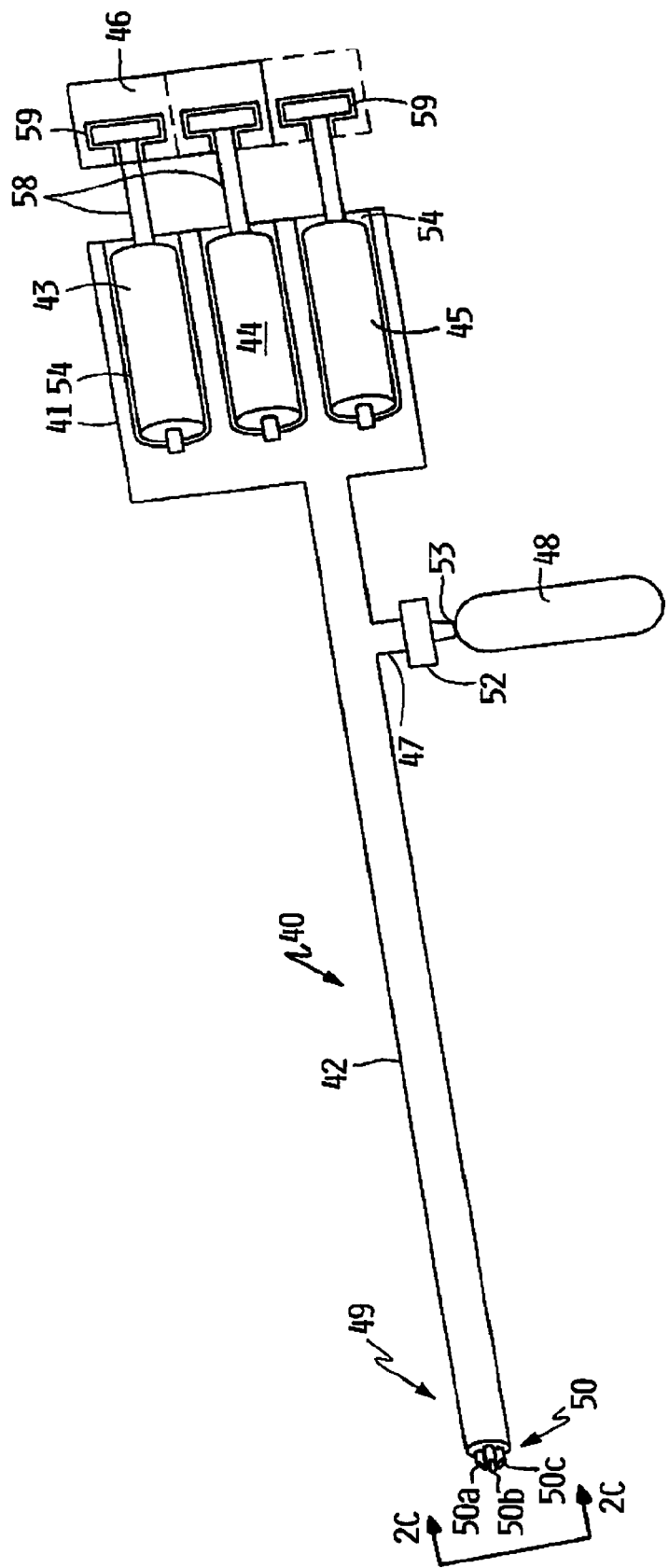
FIGS. 2A, 2B and 2C, are, respectively, a perspective view of an alternative embodiment of the two-fluid sprayer, a detailed view of the distal portion of the sprayer, and an end view of the distal portion of the sprayer taken along line 2C-2C of FIG. 2A.
Figure 2B:
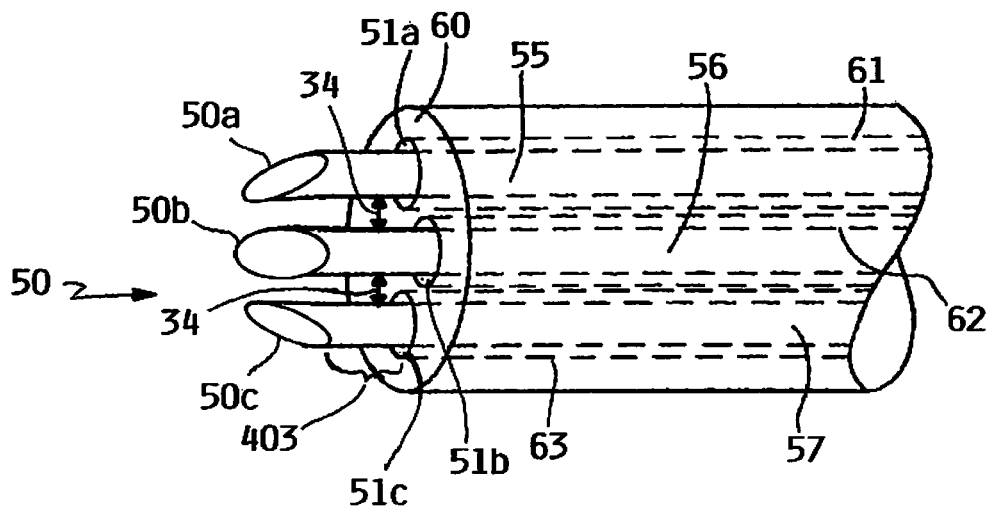
Figure 2C:
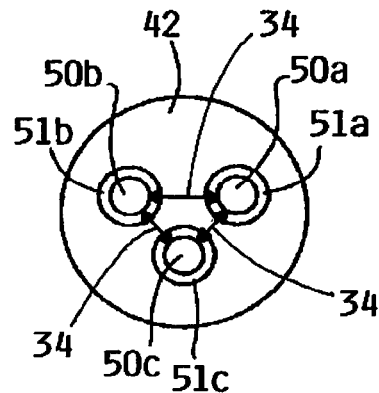

Referring now to FIGS. 2A, 2B and 2C, an alternative embodiment of a sprayer for forming materials such as adherent tissue coatings from a three-part hydrogel system is described. Sprayer 40 comprises body 41 having elongated barrel 42, syringes 43, 44, and 45, actuator 46 and gas inlet port 47 coupled compressed gas cylinder 48. Distal portion 49 of sprayer 40 includes distal tip 50 and openings 50a, 50b and 50c. Distal tip 50 also has conduits 55, 56, and 57 which are at least partially surrounded by gas flow outlets 51a, 51b and 51c, respectively. Compressed gas cylinder 48 is coupled to gas inlet port 47 via valve 52 and filter 53. Valve 52 is configured, for example, so that it may be selectively opened or closed by rotating the valve a half-turn. Filter 53 serves the same functions as filter 16a in the embodiment of FIG. 1.

Body 41 includes chambers 54 into which syringes 43, 44 and 45 are placed so that the outlets of the syringes are coupled in fluid communication with openings 50a, 50b, and 50c by conduits 55, 56 and 57, respectively. Each of syringes 43-45 includes plunger 58 that may be engaged in recesses 59 of actuator 46. Actuator 46 may link all three of plungers 58 together for common motion, or may be used to link only two of the plungers together, as illustrated by the dotted line in FIG. 2A. Actuator 46 may therefore be depressed to dispense equal volumes of crosslinkable solution from each of syringes 43-45 or just a subset thereof. As in the embodiment of FIG. 1A, the construction of sprayer 40 permits the sterile crosslinkable solutions to be stored separately in syringes 43-45, and assembled in sprayer 40 as required for a particular application.

Conduit 55 extends from the proximal end of barrel 42, where it is coupled to syringe 43, to a point slightly beyond distal endface 60 of barrel 42, where it forms opening 50a. Conduit 55 is disposed within lumen 61 that communicates with gas inlet port 47. Gas entering sprayer 40 via gas inlet port 47 flows through the annular space defined by the exterior of conduit 55 and the interior surface of lumen 61, exiting sprayer 40 through gas flow outlet 51a. As the gas, preferably air or carbon dioxide, flows through gas flow outlet 51a, it mixes with the crosslinkable solution from syringe 43 passing through opening 50a, and atomizes the crosslinkable solution into fine droplets or a mist. Conduit 56, disposed in lumen 62, and conduit 57, disposed in lumen 63, are similarly arranged to atomize crosslinkable solutions from syringes 44 and 45 in the gas flows exiting gas flow outlets 51b and 51c.

The gas flow outlet may be placed adjacent to, and proximal to, the openings for the compositions, as in FIGS. 2A and 2B, which depict gas flow outlets 51a, 51b, and 51c relative to having openings 50a, 50b, and 50c disposed in the endface of barrel 42. In this configuration, there is a gap 403 wherein gas flowing from the gas flow outlet flows past the tube that opens into an outlet, 50a, 50b, and 50c. The flowing gas tends to keep the openings clear of compositions that flow out of openings 50a, 50b, and 50c. Openings 50a, 50b, and 50c are separated from each other by a separation distance denoted by element 34. The separation distance helps to prevent cross-contamination between the compositions that exit the openings.

Figure 2D:
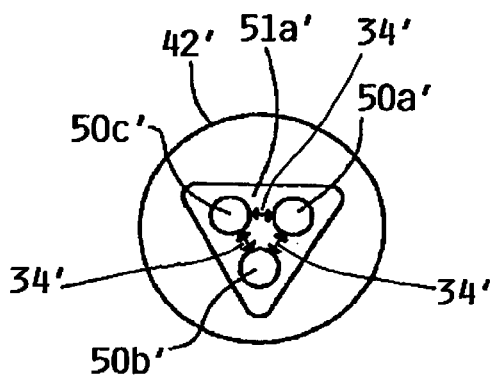
FIG. 2D is an end view of the distal portion of an alternative embodiment of the sprayer of FIG. 2A taken along line 2C-2C.

With respect to FIG. 2D, an alternative embodiment is depicted in which barrel 42' includes openings 50a', 50W and 50c' disposed within single gas flow outlet 51a' and gas flow lumen 61'. Operation of this alternative embodiment is similar to that described hereinabove, except that the crosslinkable solutions are entrained from openings 50a', 50b' and 50c' by a single stream of gas exiting gas flow outlet 51a'. In addition, like the embodiment described with respect to FIG. 1D, the sprayer may include a valve or valves for regulating the amount of crosslinkable solution and gas exiting the openings of the distal end, and also may permit a jet of gas to be directed onto a targeted tissue to displace saline or body fluids, thereby drying or cleaning the target tissue prior to instillation of the hydrogel barrier. The openings are separated from each other by a separation distance denoted by element 34 or 34'. The separation distance helps to prevent cross-contamination between the compositions that exit the openings.

The embodiments of FIG. 2 may be advantageously used to dispense a three-component hydrogel system to form a biocompatible material, e.g., an adherent therapeutic layer on a tissue surface. Alternatively, syringes 43 and 44 may contain components of crosslinkable solution that are activated to initiate crosslinking by mixing the two solutions. Syringe 45 may then contain a further crosslinkable solution that enhances adherence of the coating to tissue, for example, by providing a highly crosslinked network as the base coat or by helping the top coat adhere better to the tissue surface by other mechanisms.

Figure 3A:
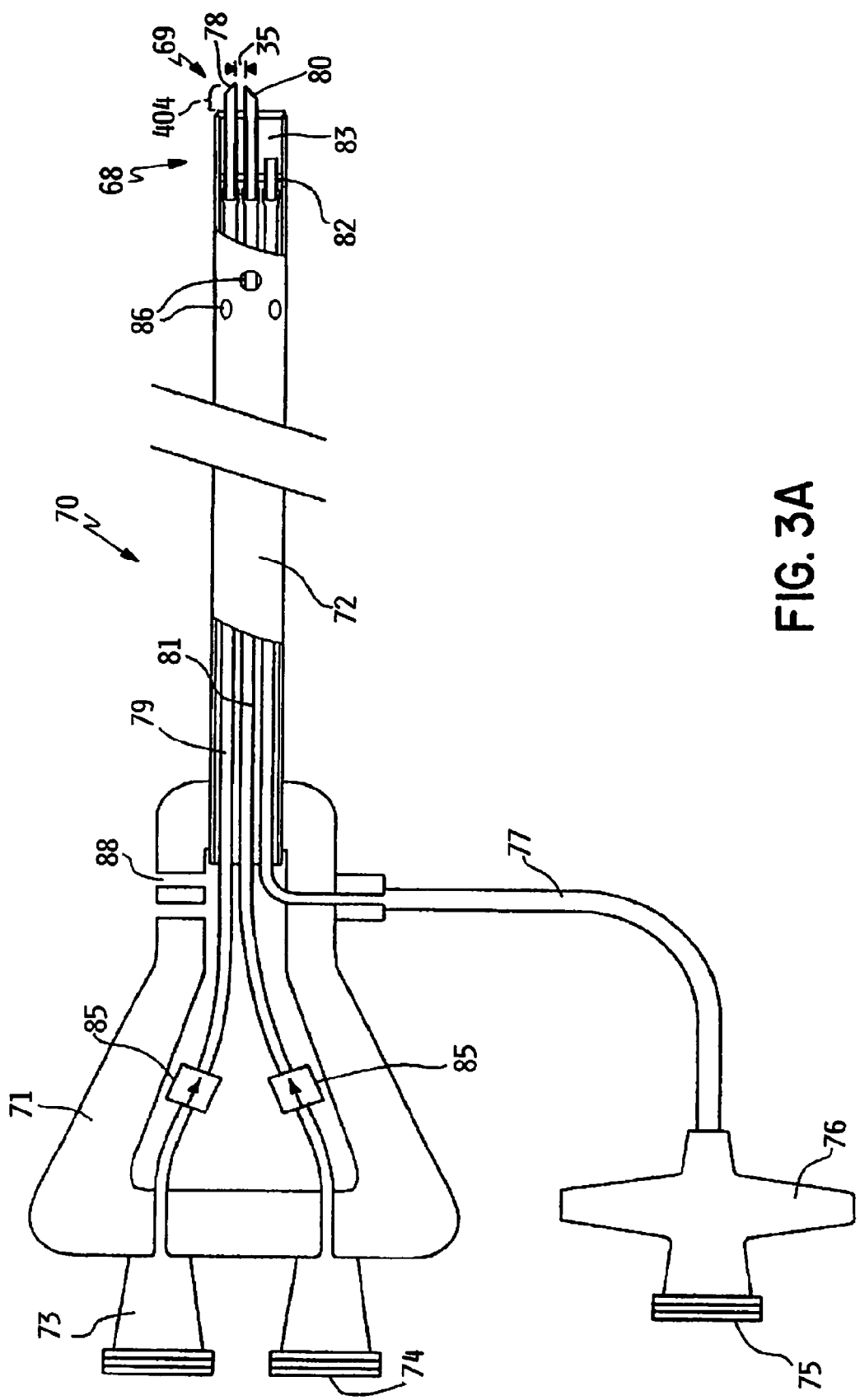
FIGS. 3A and 3B, are respectively, a partially cut-away side and a sectional end view of an alternative embodiment suitable for use in laparoscopic applications.
Figure 3B:
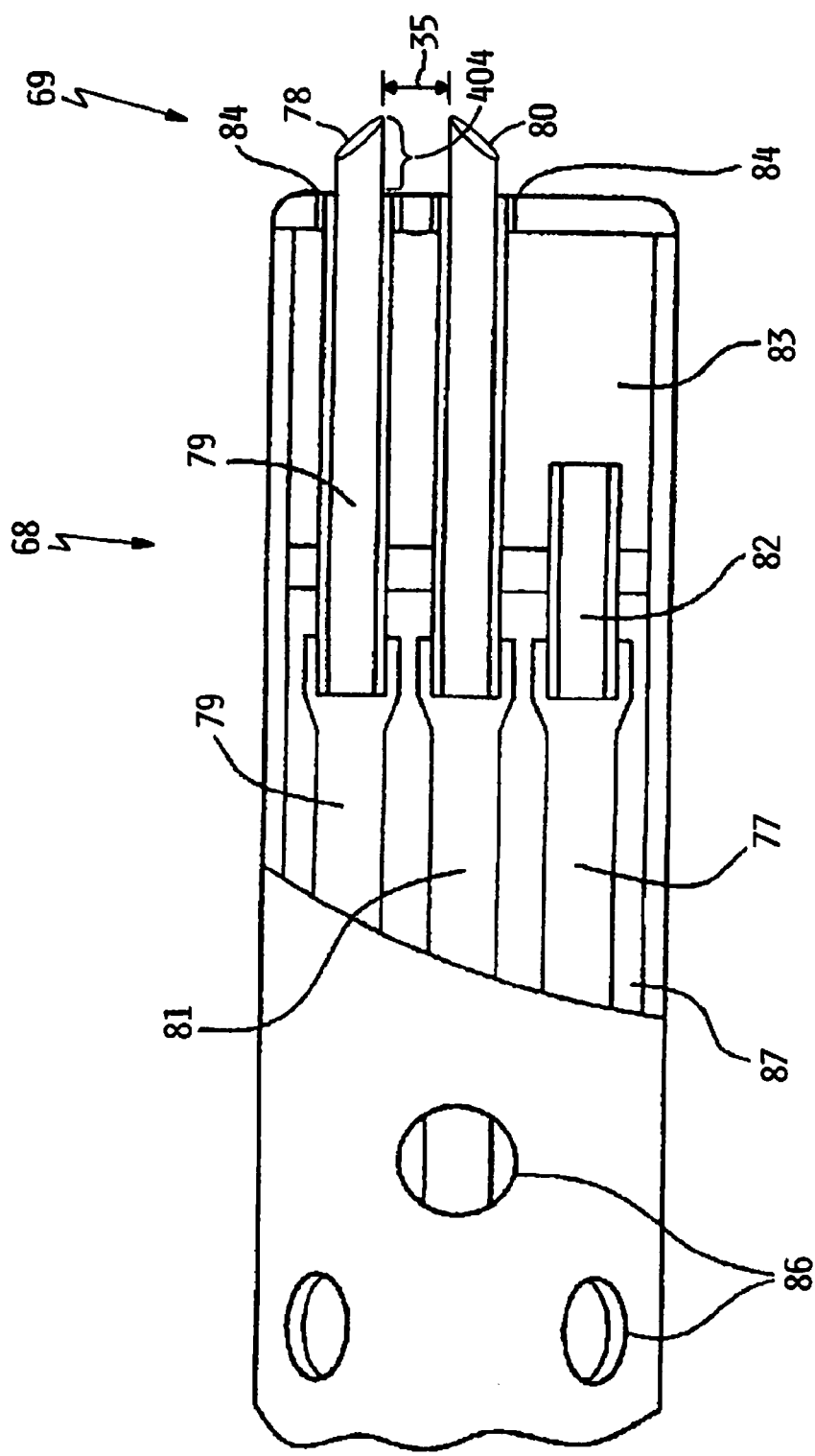

Referring now to FIGS. 3A and 3B, a further alternative embodiment of the sprayer is described which is adapted for use in laparoscopic applications. Sprayer 70 comprises-body 71 having elongated barrel 72, a distal portion 68 containing a distal tip 69, material supply ports 73 and 74, an actuator (not shown) and gas inlet port 75 coupled to a source of compressed gas or a compressor (not shown) via filter 76 and flexible hose 77. Supply port 73 is coupled to opening 78 by supply line 79 while supply port 74 is coupled to opening 80 by supply line 81. Gas inlet port 75 is coupled by hose 77 to gas flow 82 disposed in chamber 83. Gas exiting gas flow outlet 82 flows into chamber 83, and then exits chamber 83 by flowing through gas flow outlet 84 surrounding openings 78 and 80, as for the embodiment of FIG. 1.

Reservoirs of crosslinkable solutions are coupled to supply ports 73 and 74, so that when sprayer 70 is actuated, compressed gas flowing around openings 78 and 80 draws the crosslinkable solutions through supply lines 79 and 81. The gas flow exiting through annular gaps 84 atomizes and mixes the crosslinkable solution, and deposits the crosslinkable solutions onto a target tissue.

In accordance with one embodiment, one-way valves 85 are disposed on supply lines 79 and 81 to prevent backflow of insufflation gases in a tissue cavity from charging the reservoirs of crosslinkable solutions. More specifically, one-way valves permit flow through the supply lines from the reservoirs to openings 78 and 80, but prevent the backflow of insufflation gases in a tissue cavity from flowing into the reservoirs when the sprayer is first introduced into the tissue cavity. Additionally, one-way valves prevent compressed gas from the sprayer from being directed through the supply lines if, for example, if the distal end of the sprayer were pushed into tissue or otherwise blocked.

During laparoscopic surgery, for example, in the peritoneal cavity, it is typical to employ an insufflator to create a gas-filled cavity in which the surgeon can view and manipulate his or her instruments. Such devices inject a pressurized gas, such as carbon dioxide, and monitor and regulate the insufflation pressure by adding additional carbon dioxide to compensate for any leakage. Once a patient is insufflated, experienced surgeons typically maintain the insufflation without requiring much additional carbon dioxide.

Because the methods and apparatus of the present invention employ a pressurized gas to atomize and deposit the crosslinkable solution, however, a vent system must be provided to prevent excessive distension of the tissue cavity. Accordingly, sprayer 70 includes one or more vent holes 86 that communicate with bore 87 of elongated barrel 72 and proximal vent holes 88 in body 71. Vent holes 86 and proximal holes 88 permit excess gas pressure to be vented from the tissue cavity through the sprayer. While carbon dioxide will leak from the peritoneal cavity through vent holes 86 and 88, when there is no gas flow from the sprayer, applicants do not expect this leakage to present a problem, because the insufflator will add additional carbon dioxide to compensate for this leakage.

In operation, sprayer 70 is coupled to a source of compressed gas or a compressor via filter 76 and hose 77. Reservoirs of crosslinkable solutions are coupled to supply ports 73 and 74. The distal end of sprayer 70 then is disposed within a body cavity, for example, intraoperatively in the abdomen or laparoscopically in the pneumoperitoneum, a few inches from tissue to be coated. When sprayer 70 is actuated, for example, by a footpedal (not shown) coupled to the compressor or source of compressed gas, crosslinkable solutions from openings 78 and 80 by gas exiting through gas flow outlets 84. As the solutions emerge from openings 78 and 80, they are atomized and mixed, and directed onto the tissue to be coated. As a result of crosslinking, for example, induced by free radical or chemical crosslinking, the solutions form a film that adheres to the tissue to provide a therapeutic benefit.

Openings 78 and 80 are preferably arranged so that the atomized crosslinkable solutions converge to provide a spray containing a mixture of the crosslinkable solutions. Openings 78 and 80 may extend beyond distal endface 60 of barrel 72 to form gap 404, which assists to prevent clogging of the openings. The distal tip of sprayer 70 is angled, with adjacent openings 78, 80 defining an angle of about 100 degrees. The openings are separated from each other by separation distance 35 to provide a separation that decreases opportunities for cross-contamination between the openings.

Figure 4A:
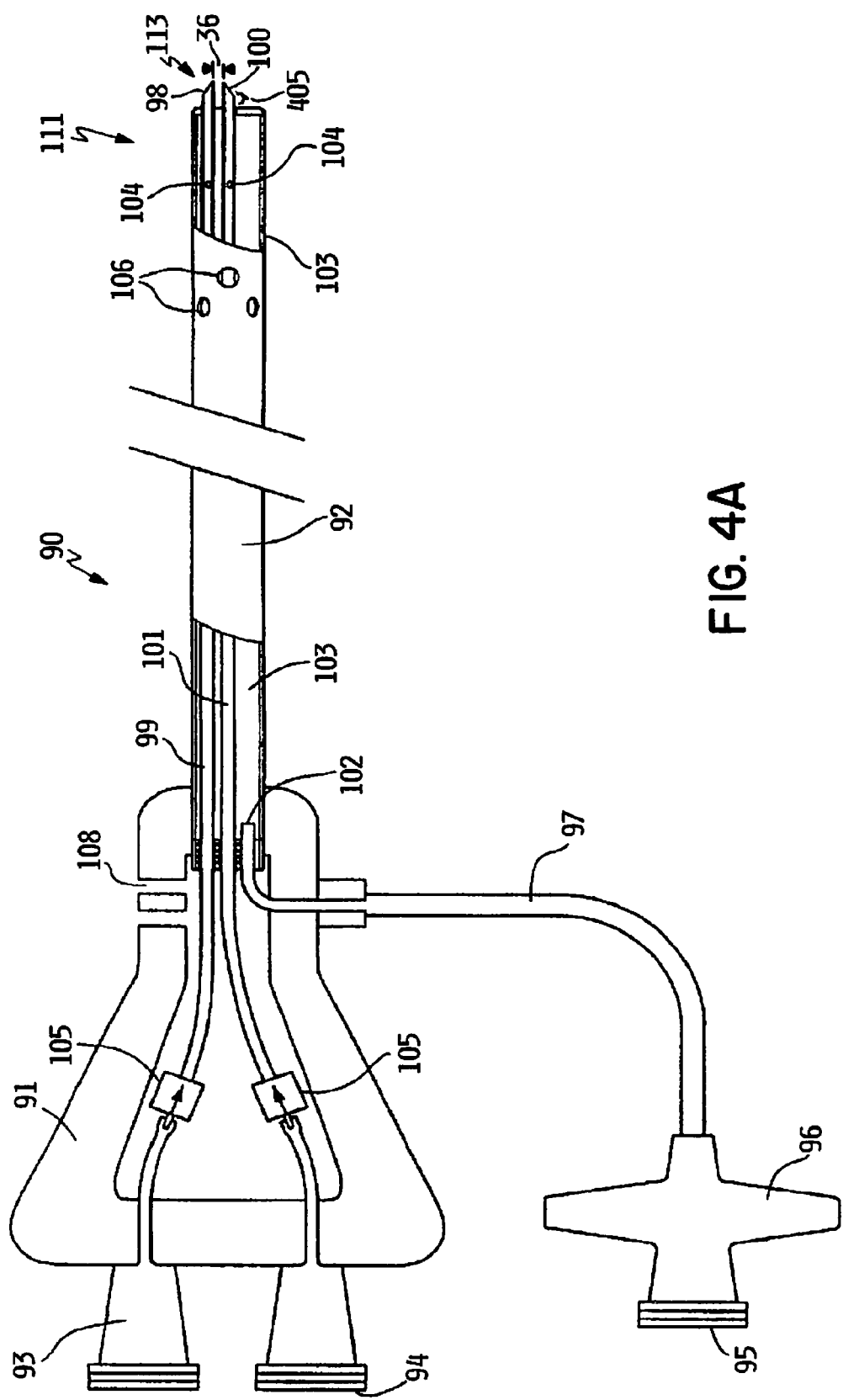
FIGS. 4A and 4B, are respectively, a partially cut-away side and a sectional end view of a further alternative embodiment suitable for use in laparoscopic applications.
Figure 4B:
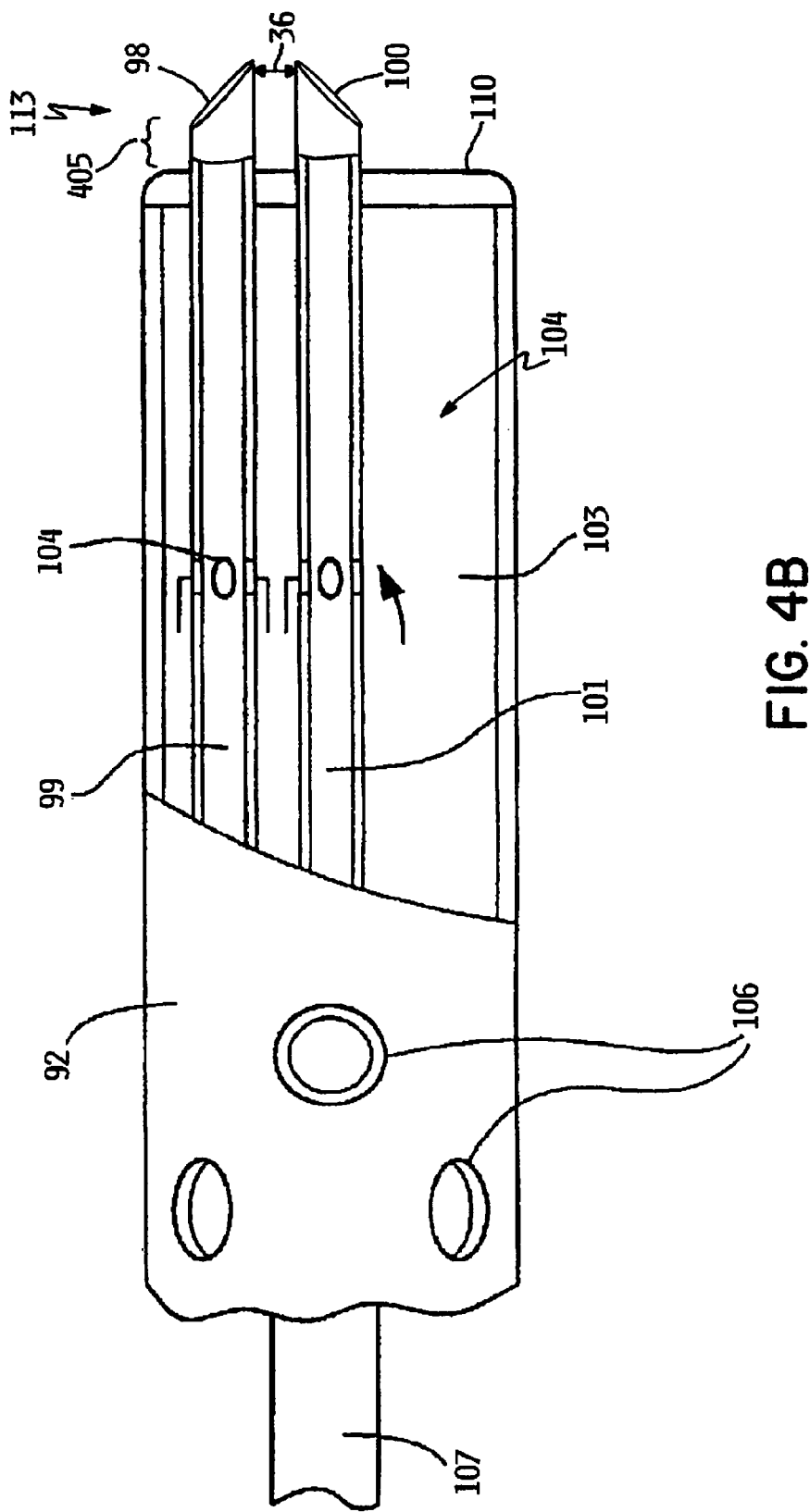
Figure 5B:
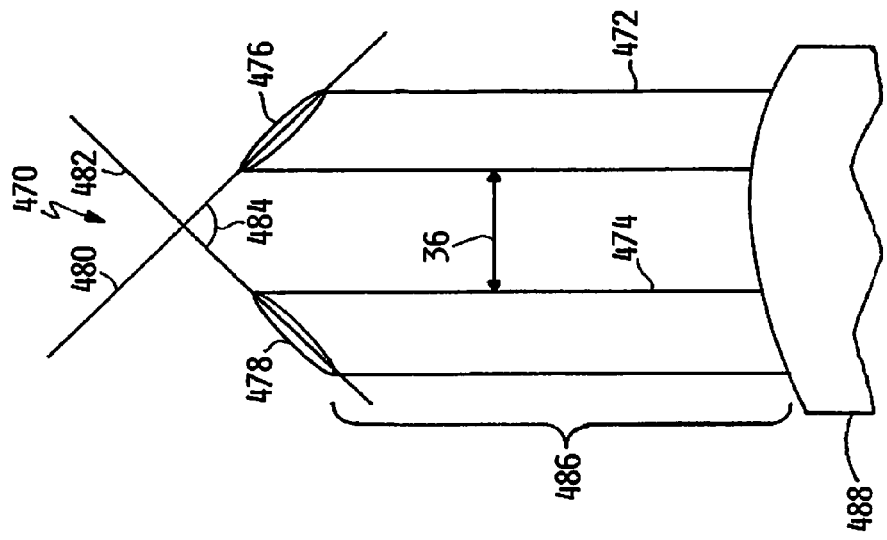
FIGS. 5A and 5B, respectively, are elevated views of alternative embodiments of an angled tip having adjacent conduits that each terminate in an exit opening for dispensing a composition.
Figure 5A:
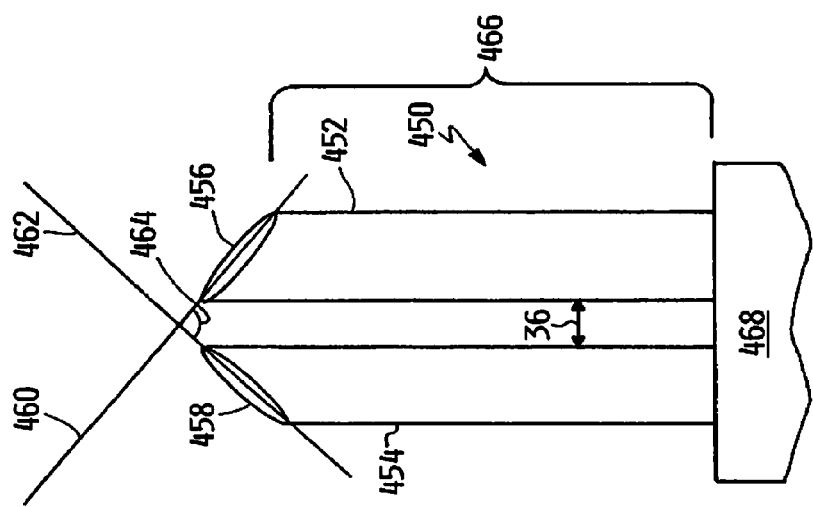

Referring to FIGS. 4A and 4B, another alternative laparoscopic embodiment of the sprayer is described. Sprayer 90 comprises body 91 having elongated barrel 92, a distal portion 111 containing a distal tip 113, material supply ports 93 and 94, an actuator (not shown) and gas inlet port 95 coupled to a source of compressed gas or a compressor (not shown) via filter 96 and flexible hose 97. Supply port 93 is coupled to opening 98 by supply line 99 while supply port 94 is coupled to opening 100 by supply line 101. Gas inlet port 95 is coupled by hose 97 to outlet 102 disposed in chamber 103. Gas exiting outlet 102 flows into chamber 103 and then exits chamber 103 by flowing through openings 104 into supply lines 99 and 101.

Reservoirs of crosslinkable solutions are coupled to supply ports 93 and 94, so that when sprayer 90 is actuated, gas introduced into chamber 103 enters supply lines 99 and 101 through openings 104, mixes with and atomizes the crosslinkable solutions in the supply lines, and propels the solutions to exit through openings 98 and 100. As the gas flow and solution mixture exits through openings 98 and 100, it further atomizes and mixes the crosslinkable solutions, and deposits the solutions onto a target tissue. The openings 98 and 100 are arranged so as to have a distal tip 113 as described hereinabove.

One-way valves 105 may be disposed on supply lines 99 and 101 to prevent backflow of gas from chamber 103 or insufflation gases in a tissue cavity from charging the reservoirs of crosslinkable solutions. More specifically, one-way valves permit flow through the supply lines from the reservoirs to nozzles 98 and 100, but prevent the backflow of insufflation gases in a tissue cavity from flowing into the reservoirs when the sprayer is first introduced into the tissue cavity. Additionally, one-way valves prevent compressed gas from chamber 103 of the sprayer from being directed through the supply lines if, for example, if the distal end of the sprayer were pushed into tissue or otherwise blocked.

In addition, sprayer 90 includes one or more vent holes 106 that communicate via tubing 107 disposed within elongated barrel 92 and proximal vent holes 108 in body 91. Vent holes 106 and proximal holes 108 permit excess gas pressure to be vented from the tissue cavity through the sprayer. While carbon dioxide will leak from the peritoneal cavity through vent holes 106 and 108 when there is no gas flow from the sprayer, applicants do not expect this leakage to present a problem, because the insufflator will add additional carbon dioxide to compensate for this leakage.

In operation, sprayer 90 is coupled to a source of compressed gas or a compressor via filter 96 and hose 97. Reservoirs of crosslinkable solutions are coupled to supply ports 93 and 94. The distal portion 111 of sprayer 90 then is disposed within a body cavity, for example, intraoperatively in the abdomen or laparoscopically in the pneumoperitoneum, a few inches from tissue to be coated. When sprayer 90 is actuated, for example, by a footpedal (not shown) coupled to the compressor or source of compressed gas, gas flows into chamber 103 and through openings 104, mixes with crosslinkable solutions in supply lines 99 and 101, and exits from openings 98 and 100 of distal tip 113. As the gas-solution mixtures emerge from openings 98 and 100, they are further atomized and mixed, and directed onto the tissue to be coated. As a result of crosslinking, for example, induced by free radical or chemical crosslinking, the solutions form a film that adheres to the tissue to provide a therapeutic benefit.

Openings 98 and 100 are preferably arranged so that the atomized crosslinkable solutions converge to provide a spray containing a mixture of the crosslinkable solutions. Adjacent openings 98 and 100 extend beyond distal endface 110 of barrel 92, to define gap 405, which assists in preventing clogging of the openings. Also, distal tip 113 is an angled tip, with an angle of about 80 degrees being defined by openings 98, 100. The openings are separated from each other by a separation distance 36, which reduces opportunities for the openings to be fouled by unwanted reaction of complements that flow through the openings.

In some embodiments, it is advantageous to reduce clogging of openings by placing the gas outlet around or near the openings for the compositions, and extending the conduits several millimeters beyond the gas outlet before terminating the conduits in the openings for the compositions. The gap between the openings and the gas flow outlet may be, e.g., between about 0.2 mm and about 10 mm; a person of ordinary skill in the arts will appreciate that all values and ranges within this range are contemplated, e.g., between about 0.25 mm and about 7.0 mm, and from about 0.5 mm to about 0.75 mm.

Referring to FIG. 1, for example, conduits 24 and 25 pass through gas flow outlets 21*a* and 21*b*. The distance between endface 28 of barrel 12 openings 20*a* or 20*b* defines a gap 402. The distance of gap 402 may be, e.g., between about 0.50 mm and about 0.75 mm, or about 0.10 mm and about 2.5 mm. Any amount of gap results in a reduction of surface tension that holds the precursor to the distal tip; however, too much gap results in the airflow not effectively blowing the polymer off of the distal tip, and can result in problems such as occlusions or divergent streams emerging from partially blocked flow paths.

In an applicator such as a sprayer with a gas flow outlet disposed around or near the openings for the compositions that are dispensed, the gas flow rate may also affect the quality and mixing of the material formed from the compositions. A gas flow rate that is too high may result in a rush of gas that will blow the hydrogel from the target location, and a gas flow rate that is too low may result in the distal tip becoming occluded. As described below, e.g., Example 3, a gas flow rate may advantageously be controlled between about 0.2 to about 1.0 liters per minute. An air flow rate of 0.6 liters per minute was particularly useful in mixing of the emergent fluids, producing a consistent material, and minimizing clogging at the distal tip.

Example 2 shows the results of experiments with various angled tips. The openings defined angles between 120 degrees and 60 degrees, with the lower angles being more effective. This result suggests that angles of less than 120 degrees are desirable in the particular devices that were tested. In other embodiments, however, variations in the relevant flow rates and relative positions of the openings and/or outlets relative to each other may be expected to be effective at angles of more than 120 degree. Thus, angles of less than, e.g., 180, 160, 140, 130, and 120 degrees are contemplated.

FIG. 5 shows embodiments of an angled tip as described herein. FIG. 5A shows angled tip 450 having adjacent conduits 452, 454, terminating in exit openings 456, 458, respectively, that are fitted with planes 460, 462, that intersect to define angle 464, which is about 90 degrees. Gap 466 is defined between opening 456 and end of barrel 468. Element 36 points to the separation distance between the openings. FIG. 5B shows angled tip 470 having adjacent conduits 472, 474, terminating in exit openings 476, 478, respectively, that are fitted with planes 480, 482, that intersect to define angle 484, which is about 100 degrees. Gap 486 is defined between opening 478 and end of barrel 488. Element 36 points to the separation distance between the openings.

Referring to FIGS. 6A and 6B, the distal tip 500 has an angled portion 502 with conduits 504, 506 that terminate in exit openings 508, 510, respectively, that define angle 511, which is depicted as being about 90 degrees. Sheath 512 encompasses conduits 504, 506, to define gas outlet 514. Gap 516 is disposed between end of sheath 512 and openings 508 or 510. The first exit opening is the terminus of a first conduit, the second exit opening is the terminus of a second conduit, a sheath surrounds at least a portion of the first conduit and the second conduit, and the gas flow outlet is defined by the space(s) between first opening, the second opening, and an opening of the sheath through which the first conduit and the second conduit pass. The sheath may be any mechanically suitable material, e.g., a flexible plastic tubing that fits snugly around the conduits.

The applicators can be made for bending of the conduits, either by a user or pre-bent at the point of manufacture. The conduits and sheath may be made of bendable material that is bendable without collapsing or kinking the conduits. For example, conduits 504 and 506 may be fabricated from a stiff yet bendable material such as PEEK or nylon and sheath 512 may be fabricated from a flexible polymer such as silicone, so that conduits 504 and 506 may be bent to certain angles and retain the bend angle without collapse of the conduits. Bending the conduits can facilitate access to target tissue in hard to reach places of the body. A variety of materials are available so that the lumen of the conduit remains open when the conduits are bent to angles up to 90°. The sprayer may be made to keep the conduits substantially parallel along the gap distance and for some distance inside the sheath so as to promote smooth air flow exiting the tip of the sprayer.

Further, a separation distance between openings may be used to reduce clogging of the openings. The separation distance is the shortest distance between the two closest portions of the two openings. For instance, two openings each have a circumference, and the shortest distance between them would be a shortest distance between any point on one circumference and any point on the other circumference. The separation distance may be, e.g., less than about 4 mm; a person of ordinary skill in the arts will appreciate that all values and ranges within 0 and 4 mm are contemplated. A smaller separation distance, however, facilitates mixing of components exiting the openings. Referring to FIGS. 6A, 6B, and 6C, keeping spacing 503 to a minimum, and preferably at zero, facilitates mixing of the hydrogel components. If spacing, 503, becomes too large, the components of the hydrogel are pushed away from each other in the gas emanating from gas outlet 514 and do not mix well.

Figure 6A:
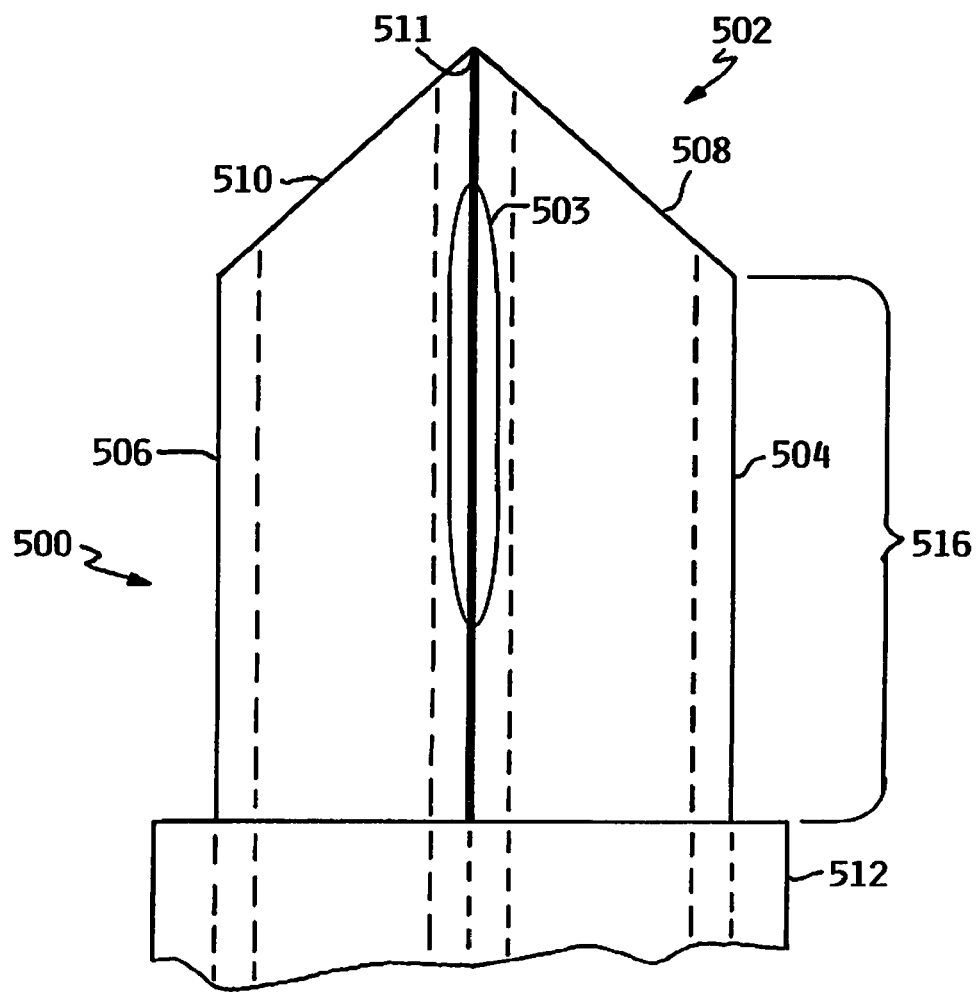
FIGS. 6A and 6B, respectively, are an elevated view of an angled tip for an applicator and a top view of the same angled tip having adjacent conduits that each terminate in an exit opening for dispensing a composition.
Figure 6B:
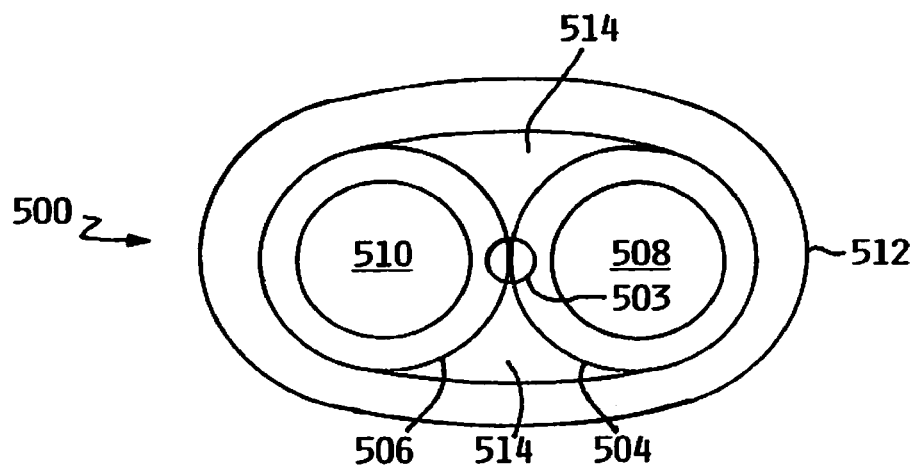
Figure 6C:
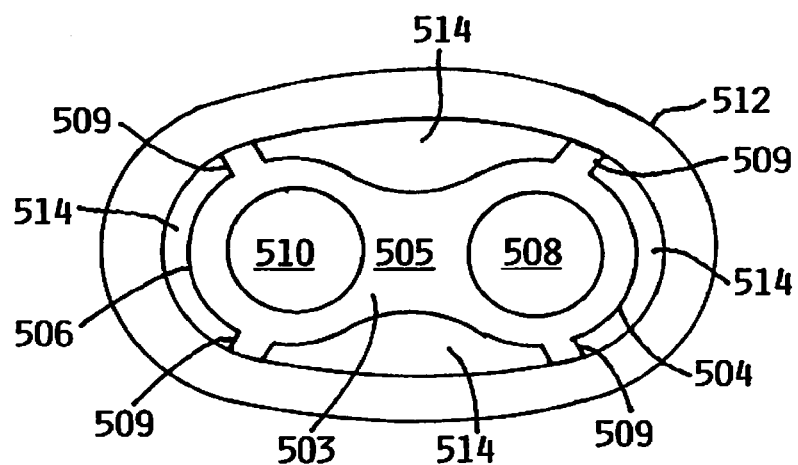
FIG. 6C is a top view of an alternative embodiment of an angled tip.

Alternatively, the flow of gas between the openings may be reduced to enhance mixing of components flowing from the openings. One approach is to block the flow of gas in the space between the openings. One approach is to shape the gas flow outlets so that the flow of gas from the outlets is minimized in the area between the openings. Another approach is to introduce a bridge, or other piece that fits into the area between the openings to fully or partially block flow in that area. As shown in FIG. 6C, one-piece bridge 505 is placed between openings 508 and 510. Mixing is enhanced due to a region of low pressure between openings 508 and 510 created as gas exits gas outlet 514. The hydrogel components are drawn towards the low-pressure region, and thus towards each other, promoting mixing. Further, gas flowing from gas outlet 514 around bridge 505 will tend to push the components towards each other as they exit from openings 508 and 510. In some embodiments, there is essentially no gas flowing in the area between the openings and the area has no openings allowing gas flow, e.g., as in FIG. 6C.

The size and shape of the gas flow outlet may be varied to control the spray pattern and the mixing of the hydrogel components. One process for making the gas flow outlets is to extrude or fit the sheath around the conduits. In this process, spacers may be used to control the dimensions of the gas conduit. For example, referring to FIG. 6C, the width of gas outlet 514 may be varied through the use of spacers, 509, extruded along the outside of conduits 504 and 506, and along bridge 505.

The components of the applicator that are exposed to the precursors may be made from materials that are not adhesive for the precursors. For example, fabricating the sheath, 512, from a hydrophobic material such as silicone is additionally beneficial to the objective of preventing clogging of the sprayer as many biomaterials and especially hydrogels will not adhere to silicone.

Hydrogel Systems for Use in an Applicator

Crosslinkable solutions preferred for use in accordance with the principles of the present invention include those that may be used to form coatings on tissue, and may form physical crosslinks, chemical crosslinks, or both. Physical crosslinks may result from complexation, hydrogen bonding, desolvation, Van der Waals interactions, ionic bonding, etc., and may be initiated by mixing two components that are physically separated until combined in situ, or as a consequence of a prevalent condition in the physiological environment, such as temperature, pH, ionic strength, etc. Chemical crosslinking may be accomplished by any of a number of mechanisms, including free radical polymerization, condensation polymerization, anionic or cationic polymerization, step growth polymerization, etc.

Hydrogels suitable for use in accordance with the principles of the present invention preferably crosslink spontaneously without requiring the use of a separate energy source. Such systems allow good control of the crosslinking process, because gelation does not occur until the sprayer is actuated and mixing of the two solutions takes place. If desired, one or both crosslinkable solutions may contain dyes or other means for visualizing the hydrogel coating. Alternatively, a colored compound may be produced as a byproduct of the reactive process. The crosslinkable solutions also may contain a bioactive drug or therapeutic compound that is entrapped in the resulting coating, so that the coating becomes a drug delivery layer.

Properties of the hydrogel system, other than crosslinkability, preferably should be selected according to the intended application. For example, if the sprayer is to be used to provide a tissue adherent coating in the abdominal cavity to prevent post-surgical tissue adhesion, it is preferable that the hydrogel system have a relatively low tensile strength, to avoid adversely effecting normal physiologic processes of the organs, be near equilibrium hydration when formed, experience relatively little in situ swelling, and be biodegradable.

Other applications may require different characteristics of the hydrogel system. There is extensive literature describing the formulation of crosslinkable coating materials for particular medical applications, which formulae may be readily adapted for use herein with little experimentation. More generally, for example, if a hydrogel system is to be used for coating of tissues, cells, medical devices, or capsules, for drug delivery or as mechanical barriers or supports, the materials should be selected on the basis of exhibited biocompatibility and lack of toxicity. For all biologically-related uses, toxicity must be low or absent in the finished state for externally coated non-living materials, and at all stages for internally-applied materials.

Additionally, the hydrogel system solutions should not contain harmful or toxic solvents. Preferably, the solutions are substantially soluble in water to allow application in a physiologically-compatible solution, such as buffered isotonic saline. Water-soluble coatings may form thin films, but more preferably form three-dimensional gels of controlled thickness. It is also preferable in cases that the coating be biodegradable, so that it does not have to be retrieved from the body. Biodegradability, as used herein, refers to the predictable disintegration of the coating into molecules small enough to be metabolized or excreted under normal physiological conditions.

Polymers Suitable for Physical Crosslinking

Physical crosslinking may be intramolecular or intermolecular or in some cases, both. For example, hydrogels can be formed by the ionic interaction of divalent cationic metal ions (such as Ca+2 and Mg+2) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. These crosslinks may be easily reversed by exposure to species that chelate the crosslinking metal ions, for example, ethylene diamine tetraacetic acid. Multifunctional cationic polymers, such as poly(l-lysine), poly(allylamine), poly(ethyleneimine), poly(guanidine), poly(vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. For example, poly(oxyethylene)-poly(oxypropylene) block copolymers, available under the trade name of PLURONIC, BASF Corporation, Mount Olive, N.J., are well known to exhibit a thermoreversible behavior in solution. Thus, an aqueous solution of 30% PLURONIC F-127 is a relatively low viscosity liquid at 4 degree C. and forms a pasty gel at physiological temperatures due to hydrophobic interactions. Other block and graft copolymers of water soluble and insoluble polymers exhibit similar effects, for example, copolymers of poly(oxyethylene) with poly(styrene), poly (caprolactone), poly(butadiene) etc.

Techniques to tailor the transition temperature, i.e., the temperature at which an aqueous solution transitions to a gel due to physical linking, are per se known. For example, the transition temperature may be lowered by increasing the degree of polymerization of the hydrophobic grafted chain or block relative to the hydrophilic block. Increase in the overall polymeric molecular weight, while keeping the hydrophilic: lipophilic ratio unchanged also leads to a lower gel transition temperature, because the polymeric chains entangle more effectively. Gels likewise may be obtained at lower relative concentrations compared to polymers with lower molecular weights.

Solutions of other synthetic polymers such as poly(N-alkylacrylamides) also form hydrogels that exhibit thermoreversible behavior and exhibit weak physical crosslinks on warming. During spraying of thermoreversible solutions, cooling of the solutions may be expected from evaporation during atomization. Upon contact with tissue target at physiological temperatures, viscosity is expected to increase from the formation of physical crosslinks. Similarly, pH responsive polymers that have a low viscosity at acidic or basic pH may be employed, and exhibit an increase in viscosity upon reaching neutral pH, for example, due to decreased solubility.

For example, polyanionic polymers such as poly(acrylic acid) or poly(methacrylic acid) possess a low viscosity at acidic pHs that increases as the polymers become more solvated at higher pHs. The solubility and gelation of such polymers further may be controlled by interaction with other water soluble polymers that complex with the polyanionic polymers. For example, it is well known that poly(ethylene oxides) of molecular weight over 2,000 dissolve to form clear solutions in water. When these solutions are mixed with similar clear solutions of poly(methacrylic acid) or poly(acrylic acid), however, thickening, gelation, or precipitation occurs depending on the particular pH and conditions used (for example see Smith et al., "Association reactions for poly (alkylene oxides) and poly(carboxylic acids)," Ind. Eng. Chem., 51:1361 (1959). Thus, a two component aqueous solution system may be selected so that the first component (among other components) consists of poly(acrylic acid) or poly(methacrylic acid) at an elevated pH of around 8-9 and the other component consists of (among other components) a solution of poly(ethylene glycol) at an acidic pH, such that the two solutions on being combined in situ result in an immediate increase in viscosity due to physical crosslinking.

Physical gelation also may be obtained in several naturally existing polymers too. For example gelatin, which is a hydrolyzed form of collagen, one of the most common physiologically occurring polymers, gels by forming physical crosslinks when cooled from an elevated temperature. Other natural polymers, such as glycosaminoglycans, e.g., hyaluronic acid, contain both anionic and cationic functional groups along each polymeric chain. This allows the formation of both intramolecular as well as intermolecular ionic crosslinks, and is responsible for the thixotropic (or shear thinning) nature of hyaluronic acid. The crosslinks are temporarily disrupted during shear, leading to low apparent viscosities and flow, and reform on the removal of shear, thereby causing the gel to reform.

Macromers for Covalent Crosslinking

Water soluble polymerizable polymeric monomers having a functionality>1 (i.e., that form crosslinked networks on polymerization) and that form hydrogels are referred to hereinafter as "macromers". Several functional groups may be used to facilitate chemical crosslinking reactions. When these functional groups are self condensible, such as ethylenically unsaturated functional groups, the crosslinker alone is sufficient to result in the formation of a hydrogel, when polymerization is initiated with appropriate agents. Where two solutions are employed, each solution preferably contains one component of a co-initiating system and crosslink on contact. The solutions are stored in separate compartments of a sprayer, and mix either when sprayed or on contact with the tissue.

An example of an initiating system suitable for use in the present invention is the combination of a peroxygen compound in one solution, and a reactive ion, such as a transition metal, in another. Other means for polymerization of macromers to coatings on tissue also may be advantageously used with macromers that contain groups that demonstrate activity towards functional groups such as amines, imines, thiols, carboxyls, isocyanates, urethanes, amides, thiocyanates, hydroxyls, etc., which may be naturally present in, on, or around tissue. Alternatively, such functional groups optionally may be provided in the region as part of the instilled formulation required to effect the barrier. In this case, no external initiators of polymerization are needed and polymerization proceeds spontaneously when two complementary reactive functional groups containing moieties interact at the application site.

Preferred hydrogel systems are those biocompatible multi-component systems that spontaneously crosslink when the components are mixed, but wherein the two or more components are individually stable for the duration of the deposition process. Such systems include, for example, contain macromers that are di or multifunctional amines in one component and di or multifunctional oxirane containing moieties in the other component. Other initiator systems, such as components of redox type initiators, also may be used. The mixing of the two or more solutions may result in either an addition or condensation polymerization that further leads to the formation of a coating.

Any monomer capable of being crosslinked to form a biocompatible surface coating may be used. The monomers may be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, U.S. Pat. Nos. 4,741,872 and 5,160,745 to De Luca et al., or U.S. Pat. No. 5,410,016 to Hubbell et al.

Some useful monomers are the crosslinkable, biodegradable, water-soluble macromers described in U.S. Pat. No. 5,410,016 to Hubbell et al, which is incorporated herein by reference. These monomers are characterized by having at least two polymerizable groups, separated by at least one degradable region. When polymerized in water, they form coherent gels that persist until eliminated by self-degradation. In one embodiment, the macromer is formed with a core of a polymer that is water soluble and biocompatible, such as the polyalkylene oxide polyethylene glycol, flanked by hydroxy acids such as lactic acid, having acrylate groups coupled thereto. Preferred monomers, in addition to being biodegradable, biocompatible, and non-toxic, also will be at least somewhat elastic after polymerization or curing.

It has been determined that monomers with longer distances between crosslinks are generally softer, more compliant, and more elastic. Thus, in the polymers of Hubbell, et al., increased length of the water-soluble segment, such as polyethylene glycol, tends to enhance elasticity. Molecular weights in the range of 10,000 to 35,000 of polyethylene glycol are preferred for such applications, although ranges from 3,000 to 100,000 also are useful.

In addition, coatings formed in accordance with the methods of the present invention may be formed as laminates (i.e., having multiple layers). Thus, for example, a lower layer of the laminate may consist of a more tightly crosslinked hydrogel that provides good adherence to the tissue surface and serves as a substrate for an overlying compliant coating to reactively bond thereto. Materials having lower molecular weights between crosslinks may be suitable for use as a base coating layer. Molecular weights in the range of 400 to 20,000 of polyethylene glycol are preferred for such applications, although ranges from 400 to 10,000 are more preferable.

It should be understood, however, that hydrogels that crosslink by a variety of other mechanisms, for example, by interaction of electrophilic and nucleophilic functional groups, also may be advantageously used in accordance with the principles of the present invention.

Initiating Systems

Metal ions may be used either as an oxidizer or a reductant in redox initiating systems. For example, in the Example set forth hereinbelow, ferrous ions are used in combination with a peroxide or hydroperoxide to initiate polymerization, or as parts of a polymerization system. In this case, the ferrous ions serve as a reductant. In other previously known initiating systems, metal ions serve as an oxidant.

For example, the eerie ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states.

Preferred metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide, etc., may be used.

Thermal initiating systems may be used rather than the redox-type systems described hereinabove. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Macromers for use in forming tissue coatings using the apparatus of the present invention include any of a variety of in situ crosslinkable macromers that form hydrogel compositions in vivo. These macromers may, for example, be selected from compositions that are biodegradable, crosslinkable, and substantially water soluble macromers comprising at least one water soluble region, at least one degradable region, and statistically more than 1 polymerizable region on average per macromer chain, wherein the polymerizable regions are separated from each other by at least one degradable region. Alternatively, if biodegradability is not desirable, compositions that do not contain the biodegradable segments but are substantially water soluble and crosslink in vivo under acceptable physiological conditions may be used.

Preferred compositions for use with devices as described herein are sold by CONFLUENT SURGICAL, INC., under the trademarks DURASEAL or SPRAYGEL.

Incorporation by Reference

Additional disclosure are set forth in commonly owned and assigned patents, including: U.S. Pat. No. 6,610,033 entitled "Dual Component Medicinal Polymer Delivery System and Methods of Use," U.S. Pat. No. 6,632,457 entitled "Composite Hydrogel Drug Delivery Systems," U.S. Pat. No. 6,566,406 entitled "Biocompatible Crosslinked Polymers," U.S. Pat. No. 6,179,862 entitled "Methods and Apparatus for In Situ Formation of Hydrogels," U.S. Pat. No. 6,165,201 entitled "Methods and Apparatus for In Situ Formation of Hydrogels," U.S. Pat. No. 6,673,093 entitled "Methods and Apparatus for In Situ Formation of Hydrogels," U.S. Pat. No. 6,152,943 entitled "Methods and Apparatus for Intraluminal Deposition of Hydrogels," U.S. Pat. No. 6,379,373 entitled "Methods and Apparatus for Intraluminal Deposition of Hydrogels," U.S. Pat. No. 6,689,148 entitled "Methods and Apparatus for Intraluminal Deposition of Hydrogels," U.S. Pat. No. 6,605,294 entitled "Methods of Using In Situ Hydration of Hydrogel Articles for Sealing of Augmentation of Tissue or Vessels," U.S. Pat. No. 6,514,534 entitled "Methods for Forming Regional Tissue Adherent Barriers and Drug Delivery Systems," and patent application Ser. Nos. 09/133,940; 10/639,700 entitled "Composite Hydrogel Drug Delivery Systems," Ser. No. 10/373,939 entitled "Biocompatible Crosslinked Polymers," Ser. No. 10/373,269 entitled "Biocompatible Crosslinked Polymers," Ser. No. 09/776,120 entitled "Dehydrated Hydrogel Precursor-Based, Tissue Adherent Compositions and Methods of Use," Ser. Nos. 09/147,897, 10/068,807 entitled "Crosslinking Agents and Methods of Use," Ser. No. 10/293,453 entitled "Proteinaceous Gels Having Visualization Agents and Methods of Use Thereof," Ser. No. 10/364,592 entitled "Crosslinked Albumin Hydrogels," Ser. No. 10/319,308 entitled "Adhesion Barriers Applicable By Minimally Invasive Surgery and Methods of Use Thereof," Ser. No. 10/756,181 entitled "Methods and Apparatus for Intraluminal Deposition of Hydrogels," Ser. No. 10/616,055 entitled "Methods of Using In Situ Hydration of Hydrogel Articles for Sealing or Augmentation of Tissue or Vessels," Ser. No. 10/266,980 entitled "Methods for Forming Regional Tissue Adherent Barriers And Drug Delivery Systems," and Ser. No. 10/010,715 entitled "Biocompatible Crosslinked Polymers", each of which are hereby incorporated by reference herein. These applications include, among other things, descriptions of components that may be used in the applicators described herein, e.g., including precursors for forming a hydrogel.

EXAMPLES

Example 1

Sprayer 10 of FIG. 1 is used in conjunction with aqueous solutions of crosslinkable monomers. Solution 1, consisting of a 10% solution of a polyethylene glycol diacrylate (M.W. 3,000 Da, purchased from Shearwater Polymers, Huntsville, Ala.) dissolved in normal saline (pH 5-6) and containing 500 ppm of hydrogen peroxide is drawn up in syringe 13, preferably a 5 cc syringe. Solution 2, consisting of a 10% solution of a polyethylene glycol diacrylate dissolved in normal saline (pH 5-6) and containing 5000 ppm of ferrous sulfate peroxide, is drawn up in syringe 14, also a 5 cc syringe. Syringes 13 and 14 are individually loaded in compartments 23, and are coupled to conduits 24 and 25 and actuator 15.

Airflow from a regulated source of compressed air (an air compressor such as those commercially available for airbrushes) is connected to the sprayer 10 using a piece of tubing. When actuator 15 is depressed, a steady spray of the two liquid components will be observed. When this spray is directed to a piece of tissue a hydrogel coating will be observed to form on the surface of the tissue. The hydrogel coating is resistant to rinsing and is well adhered to the tissue surface. Within a short period of time (less than a minute) an area of 10 cm. times 5 cm may be coated with ease.

Example 2

A sprayer as in sprayer 10 of FIG. 1 was mounted in a rigid system in a horizontal position for a horizontal spray test. The sprayer was essentially identical to sprayer 10, except that the gas flow outlets and conduits were arranged as depicted in FIGS. 6A, 6B. The angle 511, and was about 90 degrees, sheath 512 was made of plastic, and encompassed conduits 504, 506, to define gas outlet 514. Gap 516 was about 0.7 mm.

The tip of each sprayer was a distance of 2 cm from the target location, a vertical mylar sheet. In each of the syringes 13 and 14 was placed 1 mL of DuraSeal® sealant. Plungers 26 were depressed to dispense 0.2 mL (0.1 mL per syringe). The sprayer 10 was left to stand for 30 seconds. Then an additional 0.2 mL (0.1 mL per syringe) increment was delivered. This was repeated until the entire polymer was delivered in 0.2 mL increments with 30 seconds of standing between each application. The same procedure was followed for sprayer 10 that contained a straight or flat surface distal tip and for sprayer 10 that contained an angled shape distal tip (90 degrees).

Figure 7A:
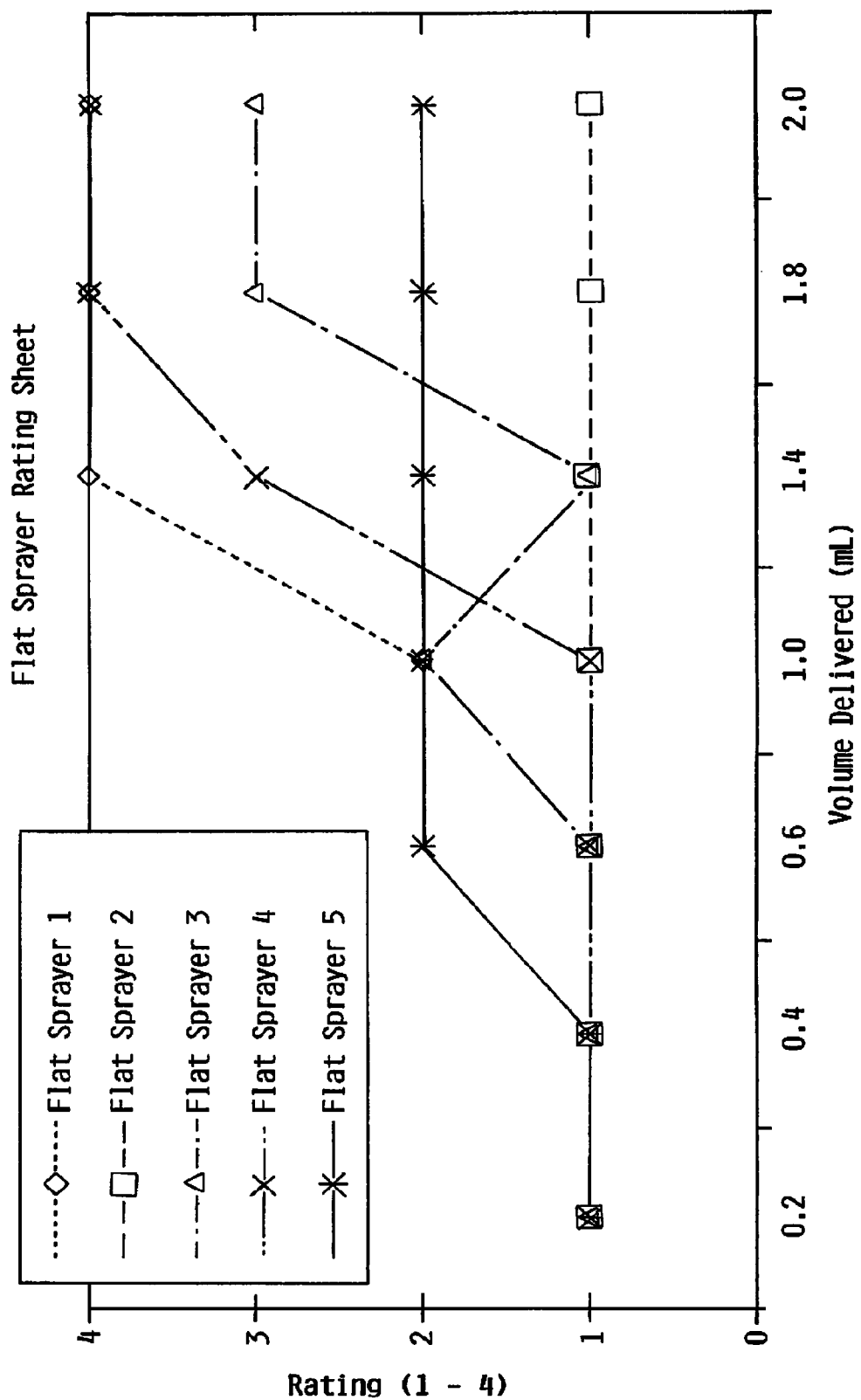
FIG. 7A is a graphical view rating the function of flat sprayers.
Figure 7B:
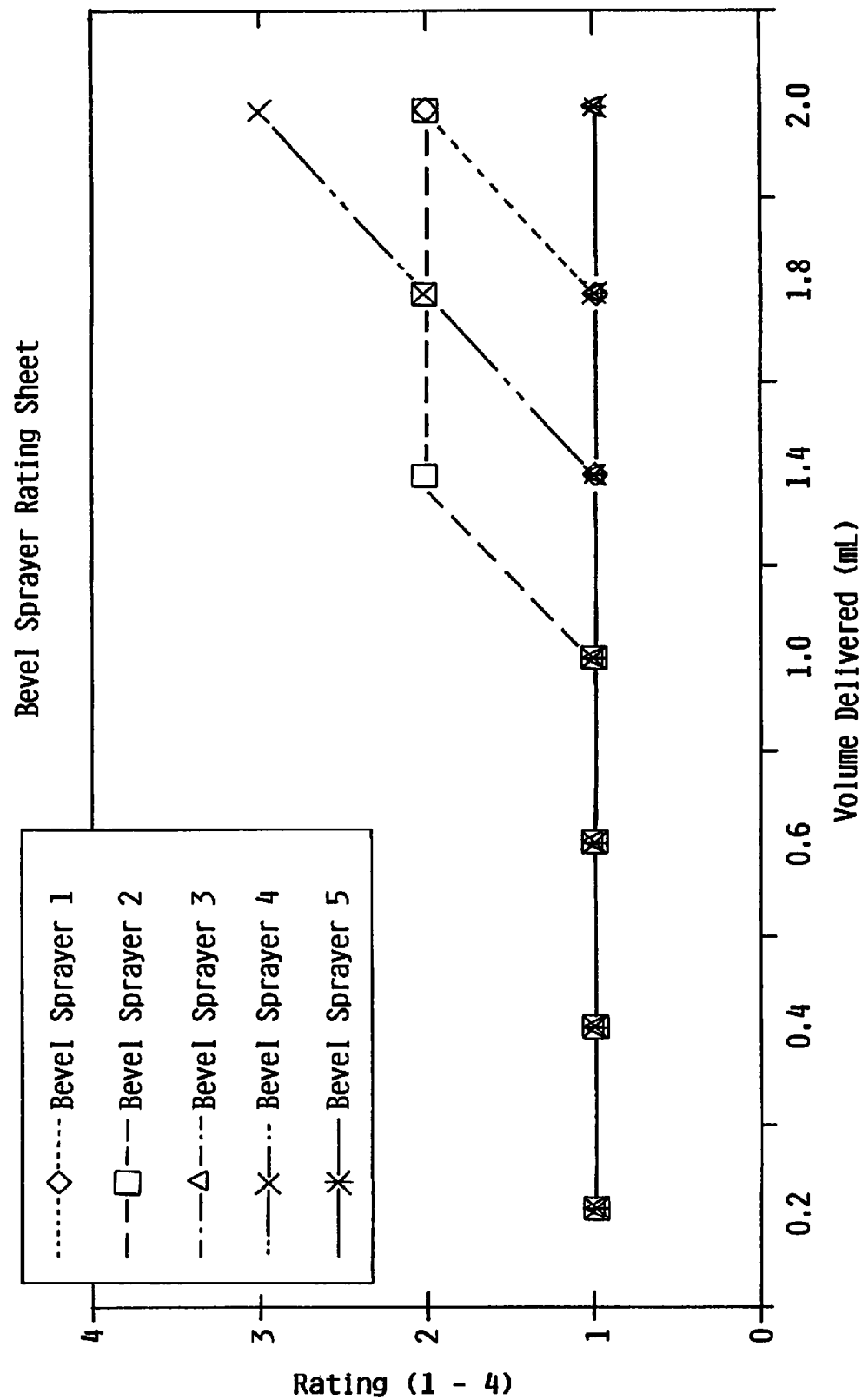
FIG. 7B is a graphical view rating the function of angled shape sprayers.

After each increment application, the sprayer 10 was rated using a scoring system to determine the function with respect to clogging. The scoring system was: (1) near perfect (good spray/good gel quality); (2) slight plugging (can be unplugged and continue working by depressing syringes); (3) divergent streams; and (4) one or more openings 20a or 20b of distal tip 20 occluded. The results of this test were graphed as illustrated in FIGS. 7A and 7B.

The angle between the openings on the angle tip was further adjusted to determine what angles would be most suitable. A sprayer was tested at a variety of flow rates with different angles of 60, 90, and 120 degrees. The 120 degree angle had some difficulties with clogging. The 60 and 90 degree angles performed well, and were similar in effectiveness.

Example 3

Sprayers were tested to determine the air flow required to achieve both good mixing and good material formation from the compositions. Sprayers as in Example 2 were mounted vertically in a rigid fixture suspended 4 cm form a target of mylar. The sprayers were connected to an air source with a regulator, and the mass flow of the air was adjusted to range between 0.2 to 1.0 liters/minute. A total volume of 0.4 ml of the material formed from the precursors was deposited on the target at each flow rate. The pattern of material formed on the target was observed. At 1.0 l/min, the material was deposited in a volcano-shape, i.e., a circle with relatively more material deposited around the edges of the circle. At rates below 0.4 l/minute, the applicator tended to clog. The 0.6 ml/minute rate made a pattern that was relatively more consistent in thickness and quality compared to 0.8 ml/minute rate, which showed a more significant volcano effect.

All patents, publications, and journal articles set forth herein are hereby incorporated by reference herein.

We claim:

1. A medical apparatus for applying a biocompatible coating in situ, the apparatus comprising:
an elongated barrel having a distal end defining a gas flow outlet; and
first and second conduits each having a distal end extending through the gas flow outlet and beyond the distal end of the elongated barrel, the first conduit defining a first exit opening and the second conduit defining a second exit opening, the first and second conduits being configured to deliver a first composition through the first conduit and a second composition through the second conduit, the first and second exit openings being positioned externally of the elongated barrel distally of the gas flow outlet to mix the first composition and the second composition externally of the elongated barrel and the first and second conduits, wherein the distal end of the first conduit has a first beveled tip defining the first exit opening, the first beveled tip defining a first plane having a first axis which is angled with respect to a longitudinal axis of the first conduit and the distal end of the second conduit has a second beveled tip defining the second exit opening, the second beveled tip defining a second plane having a second axis which is angled with respect to a longitudinal axis of the second conduit, the first axis intersecting the second axis at the distal end of the first and second conduits to define an interior angle that is less than about 140 degrees, the first and second beveled tips being oriented to facilitate mixing of the first and second compositions at a location distally of the first and second conduits, wherein the distal end of the first conduit is in direct physical contact with the distal end of the second conduit.

2. The apparatus of claim 1, wherein the angle is between about 120 degrees and about 30 degrees.

3. The apparatus of claim 1, wherein the interior angle defines the distal tip of the apparatus.

4. The apparatus of claim 1, wherein the distal ends of the first and second conduits are positioned in contact with one another along the longitudinal axis of the elongated barrel.

5. The apparatus of claim 1, further including one or more spacers between the first and second conduits and the elongated barrel to vary the size of the gas flow outlet.

6. The apparatus of claim 5, wherein the one or more spacers is formed along at least one of the first and second conduits.

7. The apparatus of claim 1, wherein a gas exiting the gas flow outlet propels the first and second composition out of the first and second exit openings, respectively.

* * * * *